United States Patent
Gousse et al.

(10) Patent No.: US 10,722,444 B2
(45) Date of Patent: Jul. 28, 2020

(54) STABLE HYDROGEL COMPOSITIONS INCLUDING ADDITIVES

(71) Applicant: Allergan Industrie, SAS, Pringy (FR)

(72) Inventors: Cécile Gousse, Dingy St. Clair (FR); Sébastien Pierre, Annecy (FR); Pierre F. Lebreton, Annecy (FR)

(73) Assignee: Allergan Industrie, SAS, Pringy (FR)

( * ) Notice: Subject to any disclaimer, the term of this patent is extended or adjusted under 35 U.S.C. 154(b) by 0 days.

(21) Appl. No.: 15/514,329

(22) PCT Filed: Sep. 30, 2014

(86) PCT No.: PCT/IB2014/001959
§ 371 (c)(1),
(2) Date: Mar. 24, 2017

(87) PCT Pub. No.: WO2016/051219
PCT Pub. Date: Apr. 7, 2016

(65) Prior Publication Data
US 2017/0273886 A1 Sep. 28, 2017

(51) Int. Cl.
*A61K 8/73* (2006.01)
*A61L 27/20* (2006.01)
*A61L 27/50* (2006.01)
*A61K 8/04* (2006.01)
*A61K 8/365* (2006.01)
*A61Q 19/08* (2006.01)
*A61K 8/49* (2006.01)

(52) U.S. Cl.
CPC .............. *A61K 8/735* (2013.01); *A61K 8/042* (2013.01); *A61K 8/365* (2013.01); *A61K 8/498* (2013.01); *A61L 27/20* (2013.01); *A61L 27/50* (2013.01); *A61Q 19/08* (2013.01); *A61K 2800/91* (2013.01); *A61L 2400/06* (2013.01)

(58) Field of Classification Search
CPC .... A61K 2800/91; A61K 8/042; A61K 8/365; A61K 8/498; A61K 8/735; A61Q 19/08
See application file for complete search history.

(56) References Cited

U.S. PATENT DOCUMENTS

| | | |
|---|---|---|
| 2,128,827 A | 8/1938 | Killian |
| 3,548,056 A | 12/1970 | Eigen et al. |
| 3,763,009 A | 10/1973 | Suzuki et al. |
| 3,949,073 A | 4/1976 | Daniels et al. |
| 4,060,081 A | 11/1977 | Yannas et al. |
| 4,140,537 A | 2/1979 | Luck et al. |
| 4,233,360 A | 11/1980 | Luck et al. |
| 4,273,705 A | 6/1981 | Kato |
| 4,279,812 A | 7/1981 | Cioca |
| 4,424,208 A | 1/1984 | Wallace et al. |
| 4,501,306 A | 2/1985 | Chu et al. |
| 4,582,640 A | 4/1986 | Smestad et al. |
| 4,582,865 A | 4/1986 | Balazs et al. |
| 4,605,691 A | 8/1986 | Balazs et al. |
| 4,636,524 A | 1/1987 | Balazs et al. |
| 4,642,117 A | 2/1987 | Nguyen et al. |
| 4,657,553 A | 4/1987 | Taylor |
| 4,713,448 A | 12/1987 | Balazs et al. |
| 4,716,154 A | 12/1987 | Malson et al. |
| 4,772,419 A | 9/1988 | Malson et al. |
| 4,803,075 A | 2/1989 | Wallace et al. |
| 4,886,787 A | 12/1989 | De Belder et al. |
| 4,896,787 A | 1/1990 | Delamour et al. |
| 5,009,013 A | 4/1991 | Wiklund |
| 5,087,446 A | 2/1992 | Suzuki et al. |
| 5,091,171 A | 2/1992 | Yu et al. |
| 5,143,724 A | 9/1992 | Leshchiner |
| 5,246,698 A | 9/1993 | Leshchiner et al. |
| 5,314,874 A | 5/1994 | Miyata et al. |
| 5,328,955 A | 7/1994 | Rhee et al. |
| 5,356,883 A | 10/1994 | Kuo et al. |
| 5,399,351 A | 3/1995 | Leshchiner et al. |
| 5,428,024 A | 6/1995 | Chu et al. |
| 5,531,716 A | 7/1996 | Luzio et al. |
| 5,565,519 A | 10/1996 | Rhee et al. |
| 5,571,503 A | 11/1996 | Mausner |
| 5,614,587 A | 3/1997 | Rhee et al. |
| 5,616,568 A | 4/1997 | Pouyani et al. |
| 5,616,611 A | 4/1997 | Yamamoto et al. |
| 5,616,689 A | 4/1997 | Shenoy et al. |
| 5,633,001 A | 5/1997 | Agerup |
| 5,643,464 A | 7/1997 | Rhee et al. |
| 5,676,964 A | 10/1997 | Della Valle et al. |

(Continued)

FOREIGN PATENT DOCUMENTS

| | | |
|---|---|---|
| CA | 949965 | 6/1974 |
| CA | 2805008 | 1/2012 |

(Continued)

OTHER PUBLICATIONS

Kim et al., "Gallotannin Isolated from Euphorbia Species, 1,2,6-Tri-O-galloyl-b-D-allose, Decreases Nitric . . . ", Jun. 2009, Biological and Pharmaceutical Bulletin, vol. 32, issue 6, pp. 1053-1056. (Year: 2009).*
National Center for Biotechnology Information. PubChem Compound Database; CID=370, https://pubchem.ncbi.nlm.nih.gov/compound/370 (accessed Mar. 18, 2018). (Year: 2018).*
National Center for Biotechnology Information. PubChem Compound Database; CID=689043, https://pubchem.ncbi.nlm.nih.gov/compound/689043 (accessed Mar. 18, 2018). (Year: 2018).*
Nadim et al., "Improvement of polyphenol properties upon glucosylation in a UV-induced skin cell ageing model", first published Sep. 5, 2014, International Journal of Cosmetic Science, vol. 36, pp. 579-587. (Year: 2014).*

(Continued)

Primary Examiner — Michael B. Pallay
(74) Attorney, Agent, or Firm — Nathan S. Smith; Chris Betti; Morgan, Lewis & Bockius LLP

(57) ABSTRACT

The present specification generally relates to an injectable dermal filler composition that includes crosslinked hyaluronic acid-based polymer and an antioxidant.

14 Claims, 6 Drawing Sheets

(56) References Cited

U.S. PATENT DOCUMENTS

| | | |
|---|---|---|
| 5,823,671 A | 10/1998 | Mitchell et al. |
| 5,824,333 A | 10/1998 | Scopelianos et al. |
| 5,827,529 A | 10/1998 | Ono et al. |
| 5,843,907 A | 12/1998 | Sakai et al. |
| 5,880,107 A | 3/1999 | Buenter |
| 5,886,042 A | 3/1999 | Yu et al. |
| 5,935,164 A | 8/1999 | Iverson |
| 5,972,326 A | 10/1999 | Galin et al. |
| 5,972,385 A | 10/1999 | Liu et al. |
| 5,980,930 A | 11/1999 | Fenton et al. |
| 6,013,679 A | 1/2000 | Kuo et al. |
| 6,066,325 A | 5/2000 | Wallace et al. |
| 6,129,761 A | 10/2000 | Hubbell |
| 6,224,857 B1 | 5/2001 | Romeo et al. |
| 6,335,035 B1 | 1/2002 | Drizen et al. |
| 6,372,494 B1 | 4/2002 | Naughton et al. |
| 6,383,218 B1 | 5/2002 | Sourdille et al. |
| 6,383,219 B1 | 5/2002 | Telandro et al. |
| 6,418,934 B1 | 7/2002 | Chin |
| 6,495,148 B1 | 12/2002 | Abbiati |
| 6,521,223 B1 | 2/2003 | Calias et al. |
| 6,544,503 B1 | 4/2003 | Vanderhoff et al. |
| 6,627,620 B1 | 9/2003 | Nielsen |
| 6,630,486 B1 | 10/2003 | Royer |
| 6,685,963 B1 | 2/2004 | Taupin et al. |
| 6,716,251 B1 | 4/2004 | Asius et al. |
| 6,734,298 B1 | 5/2004 | Barbucci et al. |
| 6,767,924 B2 | 7/2004 | Yu et al. |
| 6,767,928 B1 | 7/2004 | Murphy et al. |
| 6,852,255 B2 | 2/2005 | Yang et al. |
| 6,893,466 B2 | 5/2005 | Trieu |
| 6,903,199 B2 | 6/2005 | Moon et al. |
| 6,921,819 B2 | 7/2005 | Piron et al. |
| 6,924,273 B2 | 8/2005 | Pierce |
| 6,939,562 B2 | 9/2005 | Spiro et al. |
| 6,979,440 B2 | 12/2005 | Shefer et al. |
| 6,991,652 B2 | 1/2006 | Burg |
| 7,015,198 B1 | 3/2006 | Orentreich |
| 7,119,062 B1 | 10/2006 | Alvis et al. |
| 7,129,209 B2 | 10/2006 | Rhee |
| 7,166,570 B2 | 1/2007 | Hunter et al. |
| 7,192,984 B2 | 3/2007 | Berg et al. |
| 7,196,180 B2 | 3/2007 | Aeschlimann et al. |
| 7,314,636 B2 | 1/2008 | Caseres et al. |
| 7,316,822 B2 | 1/2008 | Binette |
| 7,491,709 B2 | 2/2009 | Carey |
| 7,741,476 B2 | 6/2010 | Lebreton |
| 7,767,452 B2 | 8/2010 | Kleinsek |
| 7,799,767 B2 | 9/2010 | Lamberti et al. |
| 7,875,296 B2 | 1/2011 | Binette |
| 7,902,171 B2 | 3/2011 | Reinmuller et al. |
| 8,052,990 B2 | 11/2011 | Hermitte et al. |
| 8,053,423 B2 | 11/2011 | Lamberti et al. |
| 8,124,120 B2 | 2/2012 | Sadozai et al. |
| 8,137,702 B2 | 3/2012 | Binette et al. |
| 8,153,591 B2 | 4/2012 | Masters et al. |
| 8,288,347 B2 | 10/2012 | Collette et al. |
| 8,318,695 B2 | 11/2012 | Stroumpoulis et al. |
| 8,338,375 B2 | 12/2012 | Schroeder et al. |
| 8,338,388 B2 | 12/2012 | Lebreton |
| 8,357,795 B2 | 1/2013 | Lebreton |
| 8,394,782 B2 * | 3/2013 | Stroumpoulis ........ A61K 8/042 514/54 |
| 8,394,783 B2 * | 3/2013 | Stroumpoulis ........ A61K 8/042 514/54 |
| 8,394,784 B2 | 3/2013 | Stroumpoulis et al. |
| 8,455,465 B2 | 6/2013 | Molliard |
| 8,512,752 B2 | 8/2013 | Crescenzi et al. |
| 8,513,216 B2 * | 8/2013 | Stroumpoulis ........ A61K 8/042 514/54 |
| 8,524,213 B2 | 9/2013 | Leshchiner et al. |
| 8,563,532 B2 | 10/2013 | Lebreton |
| 8,575,129 B2 | 11/2013 | Bellini |
| 8,586,562 B2 | 11/2013 | Lebreton |
| 8,853,184 B2 * | 10/2014 | Stroumpoulis ........ A61K 8/042 424/400 |
| 9,662,422 B2 | 5/2017 | Pollock et al. |
| 2001/0039336 A1 | 11/2001 | Miller et al. |
| 2002/0102311 A1 | 8/2002 | Gustavsson et al. |
| 2002/0160109 A1 | 10/2002 | Yeo et al. |
| 2003/0031638 A1 | 2/2003 | Joshi et al. |
| 2003/0093157 A1 | 5/2003 | Casares et al. |
| 2003/0119985 A1 | 6/2003 | Sehl et al. |
| 2003/0148995 A1 | 8/2003 | Piron et al. |
| 2004/0032056 A1 | 2/2004 | Vang et al. |
| 2004/0101959 A1 | 5/2004 | Marko et al. |
| 2004/0127698 A1 | 7/2004 | Tsai et al. |
| 2004/0127699 A1 | 7/2004 | Zhao et al. |
| 2004/0199241 A1 | 10/2004 | Gravett et al. |
| 2004/0265389 A1 | 12/2004 | Yui et al. |
| 2005/0013729 A1 | 1/2005 | Brown-Skrobot |
| 2005/0025755 A1 | 2/2005 | Hedrick et al. |
| 2005/0101582 A1 | 5/2005 | Lyons et al. |
| 2005/0136122 A1 | 6/2005 | Sadozai et al. |
| 2005/0142152 A1 | 6/2005 | Leshchiner et al. |
| 2005/0181007 A1 | 8/2005 | Hunter et al. |
| 2005/0186261 A1 | 8/2005 | Avelar et al. |
| 2005/0186673 A1 | 8/2005 | Geistlich et al. |
| 2005/0226936 A1 | 10/2005 | Agerup |
| 2005/0271729 A1 | 12/2005 | Wang |
| 2005/0281880 A1 | 12/2005 | Wang |
| 2005/0287180 A1 | 12/2005 | Chen |
| 2006/0029578 A1 | 2/2006 | Hoemann et al. |
| 2006/0040894 A1 | 2/2006 | Hunter et al. |
| 2006/0095137 A1 | 5/2006 | Chung et al. |
| 2006/0105022 A1 | 5/2006 | Yokokawa et al. |
| 2006/0122147 A1 | 6/2006 | Wohlrab et al. |
| 2006/0141049 A1 | 6/2006 | Lyons |
| 2006/0147483 A1 | 7/2006 | Chaouk et al. |
| 2006/0189516 A1 | 8/2006 | Yang et al. |
| 2006/0194758 A1 | 8/2006 | Lebreton et al. |
| 2006/0246137 A1 | 11/2006 | Hermitte et al. |
| 2006/0257488 A1 | 11/2006 | Hubbard |
| 2006/0286769 A1 | 12/2006 | Tsuchiya et al. |
| 2007/0026070 A1 | 2/2007 | Vonwiller et al. |
| 2007/0036745 A1 | 2/2007 | Leshchiner et al. |
| 2007/0066816 A1 | 3/2007 | Tsai et al. |
| 2007/0077292 A1 | 4/2007 | Pinsky |
| 2007/0104692 A1 | 5/2007 | Quijano et al. |
| 2007/0104693 A1 | 5/2007 | Quijano et al. |
| 2007/0203095 A1 | 8/2007 | Sadozai et al. |
| 2007/0212385 A1 | 9/2007 | David |
| 2007/0224247 A1 | 9/2007 | Chudzik et al. |
| 2007/0224278 A1 | 9/2007 | Lyons et al. |
| 2007/0298005 A1 | 12/2007 | Thibault |
| 2008/0044476 A1 | 2/2008 | Lyons et al. |
| 2008/0057091 A1 | 3/2008 | Abdellaoui et al. |
| 2008/0089918 A1 | 4/2008 | Lebreton |
| 2008/0188416 A1 | 8/2008 | Bernstein |
| 2008/0193538 A1 | 8/2008 | Kitazono et al. |
| 2008/0200430 A1 | 8/2008 | Bitterman et al. |
| 2008/0207794 A1 | 8/2008 | Wright et al. |
| 2008/0241252 A1 | 10/2008 | Lyons et al. |
| 2008/0268051 A1 | 10/2008 | Hughes et al. |
| 2008/0274946 A1 | 11/2008 | Giampapa |
| 2008/0279806 A1 | 11/2008 | Cho |
| 2008/0293637 A1 | 11/2008 | Schroeder et al. |
| 2008/0300681 A1 | 12/2008 | Rigotti et al. |
| 2009/0017091 A1 | 1/2009 | Daniloff et al. |
| 2009/0018102 A1 | 1/2009 | Moutet et al. |
| 2009/0022808 A1 | 1/2009 | Champion et al. |
| 2009/0028817 A1 | 1/2009 | Niklason et al. |
| 2009/0036403 A1 | 2/2009 | Stroumpoulis et al. |
| 2009/0042834 A1 | 2/2009 | Karageozian et al. |
| 2009/0093755 A1 | 4/2009 | Schroeder et al. |
| 2009/0098177 A1 | 4/2009 | Werkmeister et al. |
| 2009/0110671 A1 | 4/2009 | Miyata et al. |
| 2009/0110736 A1 | 4/2009 | Boutros |
| 2009/0123547 A1 | 5/2009 | Hill et al. |
| 2009/0124552 A1 | 5/2009 | Hill et al. |
| 2009/0143331 A1 | 6/2009 | Stoumpoulis et al. |
| 2009/0143348 A1 | 6/2009 | Tezel et al. |
| 2009/0148527 A1 | 6/2009 | Robinson et al. |

(56) References Cited

U.S. PATENT DOCUMENTS

| | | |
|---|---|---|
| 2009/0155314 A1 | 6/2009 | Tezel et al. |
| 2009/0155362 A1 | 6/2009 | Longin et al. |
| 2009/0162415 A1 | 6/2009 | Huang et al. |
| 2009/0169615 A1 | 7/2009 | Pinsky |
| 2009/0181104 A1 | 7/2009 | Rigotti et al. |
| 2009/0263447 A1 | 10/2009 | Asius et al. |
| 2009/0291986 A1 | 11/2009 | Pappas et al. |
| 2009/0297632 A1 | 12/2009 | Waugh |
| 2009/0317376 A1 | 12/2009 | Zukowska et al. |
| 2010/0004198 A1 | 1/2010 | Stroumpoulis et al. |
| 2010/0028437 A1 | 2/2010 | Lebreton |
| 2010/0035838 A1 | 2/2010 | Herber et al. |
| 2010/0041788 A1 | 2/2010 | Voigts et al. |
| 2010/0098764 A1 | 4/2010 | Stroumpoulis et al. |
| 2010/0098794 A1 | 4/2010 | Armand |
| 2010/0099623 A1 | 4/2010 | Schroeder et al. |
| 2010/0111919 A1 | 5/2010 | Abuzaina et al. |
| 2010/0136070 A1 | 6/2010 | Dobak et al. |
| 2010/0160948 A1 | 6/2010 | Rigotti et al. |
| 2010/0161052 A1 | 6/2010 | Rigotti et al. |
| 2010/0168780 A1 | 7/2010 | Rigotti et al. |
| 2010/0226988 A1 | 9/2010 | Lebreton |
| 2010/0247651 A1 | 9/2010 | Kestler |
| 2010/0249924 A1 | 9/2010 | Powell et al. |
| 2010/0255068 A1 | 10/2010 | Stroumpoulis et al. |
| 2010/0316683 A1 | 12/2010 | Piron et al. |
| 2011/0008406 A1 | 1/2011 | Altman et al. |
| 2011/0008436 A1 | 1/2011 | Altman et al. |
| 2011/0008437 A1 | 1/2011 | Altman et al. |
| 2011/0014263 A1 | 1/2011 | Altman et al. |
| 2011/0014287 A1 | 1/2011 | Altman et al. |
| 2011/0020409 A1 | 1/2011 | Altman et al. |
| 2011/0034684 A1 | 2/2011 | Yokokawa et al. |
| 2011/0052695 A1 | 3/2011 | Jiang et al. |
| 2011/0070281 A1 | 3/2011 | Altman |
| 2011/0077737 A1 | 3/2011 | Stroumpoulis et al. |
| 2011/0097381 A1 | 4/2011 | Altman |
| 2011/0104800 A1 | 5/2011 | Kensy et al. |
| 2011/0111031 A1 | 5/2011 | Jiang et al. |
| 2011/0118206 A1 | 5/2011 | Lebreton |
| 2011/0150823 A1 | 6/2011 | Huang |
| 2011/0150846 A1 | 6/2011 | Van Epps |
| 2011/0171286 A1 | 7/2011 | Ceclie et al. |
| 2011/0171310 A1* | 7/2011 | Gousse .................. A61L 27/20 424/488 |
| 2011/0171311 A1 | 7/2011 | Gousse et al. |
| 2011/0172180 A1 | 7/2011 | Gousse et al. |
| 2011/0183001 A1 | 7/2011 | Rosson |
| 2011/0183406 A1 | 7/2011 | Kensy |
| 2011/0189292 A1 | 8/2011 | Lebreton |
| 2011/0194945 A1 | 8/2011 | Kensy et al. |
| 2011/0224164 A1 | 9/2011 | Lebreton |
| 2011/0229574 A1 | 9/2011 | Guillen et al. |
| 2011/0295238 A1 | 12/2011 | Kensy et al. |
| 2012/0010146 A1 | 1/2012 | Han et al. |
| 2012/0034462 A1 | 2/2012 | Stroumpoulis et al. |
| 2012/0045420 A1 | 2/2012 | Van Epps et al. |
| 2012/0071437 A1 | 3/2012 | Stroumpoulis et al. |
| 2012/0076868 A1 | 3/2012 | Lamberti et al. |
| 2012/0095206 A1 | 4/2012 | Chen |
| 2012/0100217 A1 | 4/2012 | Green |
| 2012/0100611 A1 | 4/2012 | Kensy et al. |
| 2012/0156265 A1 | 6/2012 | Binette et al. |
| 2012/0164098 A1 | 6/2012 | Schroeder et al. |
| 2012/0164116 A1 | 6/2012 | Van Epps |
| 2012/0165935 A1 | 6/2012 | Van Epps |
| 2012/0172328 A1 | 6/2012 | Lebreton |
| 2012/0171265 A1 | 7/2012 | Altman et al. |
| 2012/0172317 A1 | 7/2012 | Altman et al. |
| 2012/0172985 A1 | 7/2012 | Altman et al. |
| 2012/0189589 A1 | 7/2012 | Van Epps et al. |
| 2012/0189590 A1 | 7/2012 | Van Epps et al. |
| 2012/0189699 A1 | 7/2012 | Strompoulis et al. |
| 2012/0189708 A1 | 7/2012 | Van Epps et al. |
| 2012/0190644 A1 | 7/2012 | D'este |
| 2012/0207837 A1 | 8/2012 | Powell et al. |
| 2012/0208890 A1 | 8/2012 | Gousse et al. |
| 2012/0209381 A1 | 8/2012 | Powell et al. |
| 2012/0213852 A1 | 8/2012 | Van Epps et al. |
| 2012/0213853 A1 | 8/2012 | Van Epps et al. |
| 2012/0219627 A1 | 8/2012 | Van Epps et al. |
| 2012/0225842 A1 | 9/2012 | Ceclie et al. |
| 2012/0232030 A1 | 9/2012 | Gousse et al. |
| 2012/0263686 A1 | 10/2012 | Van Epps et al. |
| 2012/0265297 A1 | 10/2012 | Altman et al. |
| 2012/0269777 A1 | 10/2012 | Van Epps et al. |
| 2012/0295870 A1 | 11/2012 | Lebreton |
| 2013/0023658 A1 | 1/2013 | Stroumpoulis et al. |
| 2013/0041038 A1 | 2/2013 | Lebreton |
| 2013/0041039 A1 | 2/2013 | Lebreton |
| 2013/0072453 A1 | 3/2013 | Gousse et al. |
| 2013/0096081 A1 | 4/2013 | Njikang |
| 2013/0116188 A1 | 5/2013 | Pollock et al. |
| 2013/0116190 A1 | 5/2013 | Pollock et al. |
| 2013/0116411 A1 | 5/2013 | Pollock et al. |
| 2013/0123210 A1 | 5/2013 | Liu |
| 2013/0129835 A1 | 5/2013 | Pollock et al. |
| 2013/0131011 A1 | 5/2013 | Lebreton |
| 2013/0131655 A1 | 5/2013 | Rigotti et al. |
| 2013/0136780 A1 | 5/2013 | Tezel et al. |
| 2013/0203696 A1 | 8/2013 | Liu |
| 2013/0203856 A1 | 8/2013 | Cho, II |
| 2013/0209532 A1 | 8/2013 | Stroumpoulis et al. |
| 2013/0210760 A1 | 8/2013 | Liu |
| 2013/0237615 A1 | 9/2013 | Meunier |
| 2013/0244943 A1 | 9/2013 | Yu et al. |
| 2013/0244970 A1 | 9/2013 | Lebreton |
| 2013/0274222 A1 | 10/2013 | Horne |
| 2013/0287758 A1 | 10/2013 | Tozzi |
| 2014/0011990 A1 | 1/2014 | Lebreton |
| 2014/0227235 A1 | 8/2014 | Kim et al. |
| 2016/0113855 A1 | 4/2016 | Njikang |

FOREIGN PATENT DOCUMENTS

| | | |
|---|---|---|
| CN | 102548590 | 7/2012 |
| EP | 273823 | 7/1988 |
| EP | 416250 | 3/1991 |
| EP | 416846 | 3/1991 |
| EP | 1247522 | 10/2002 |
| EP | 1398131 | 3/2004 |
| EP | 1419792 | 5/2004 |
| EP | 1115433 | 12/2004 |
| EP | 1532991 | 5/2005 |
| EP | 1726299 | 11/2006 |
| EP | 1932530 | 6/2008 |
| EP | 2236523 | 6/2010 |
| FR | 2733427 | 10/1996 |
| FR | 2752843 | 3/1998 |
| FR | 2920000 | 2/2009 |
| FR | 2924615 | 6/2009 |
| JP | S 55-0153711 | 11/1980 |
| JP | 2002-080501 | 3/2002 |
| JP | 2007-063177 | 3/2007 |
| KR | 20110138765 | 12/2011 |
| KR | 20130018518 | 2/2013 |
| WO | WO 86/000079 | 1/1986 |
| WO | WO 86/000912 | 2/1986 |
| WO | WO 92/000105 | 1/1992 |
| WO | WO 92/020349 | 11/1992 |
| WO | WO 96/033751 | 10/1993 |
| WO | WO 94/001468 | 1/1994 |
| WO | WO 94/002517 | 3/1994 |
| WO | WO 97/004012 | 6/1997 |
| WO | WO 98/035639 | 8/1998 |
| WO | WO 98/035640 | 8/1998 |
| WO | WO 00/001428 | 1/2000 |
| WO | WO 00/08061 | 2/2000 |
| WO | WO 00/46252 | 8/2000 |
| WO | WO 01/079342 | 10/2001 |
| WO | WO 02/005753 | 1/2002 |
| WO | WO 02/006350 | 1/2002 |
| WO | WO 02/009792 | 2/2002 |
| WO | WO 03/007782 | 1/2003 |

(56) References Cited

FOREIGN PATENT DOCUMENTS

| | | |
|---|---|---|
| WO | WO 02/017713 | 3/2003 |
| WO | WO 2004/020473 | 3/2004 |
| WO | WO 2004/022603 | 3/2004 |
| WO | WO 2004/067575 | 8/2004 |
| WO | WO 2004/073759 | 9/2004 |
| WO | WO 2004/092223 | 10/2004 |
| WO | WO 2005/040224 | 6/2005 |
| WO | WO 2005/052035 | 6/2005 |
| WO | WO 2005/067944 | 7/2005 |
| WO | WO 2005/074913 | 8/2005 |
| WO | WO 2005/112888 | 12/2005 |
| WO | WO 2006/015490 | 2/2006 |
| WO | WO 2006/021644 | 3/2006 |
| WO | WO 2006/023645 | 3/2006 |
| WO | WO 2006/048671 | 5/2006 |
| WO | WO 2006/056204 | 6/2006 |
| WO | WO 2006/067608 | 6/2006 |
| WO | WO 2007/018124 | 2/2007 |
| WO | WO 2007/070617 | 6/2007 |
| WO | WO 2007/077399 | 7/2007 |
| WO | WO 2007/128923 | 11/2007 |
| WO | WO 2007/136738 | 11/2007 |
| WO | WO 2008/015249 | 2/2008 |
| WO | WO 2008/034176 | 3/2008 |
| WO | WO 2008/063569 | 5/2008 |
| WO | WO 2008/068297 | 6/2008 |
| WO | WO 2008/072230 | 6/2008 |
| WO | WO 2008/077172 | 7/2008 |
| WO | WO 2008/098019 | 8/2008 |
| WO | WO 2008/139122 | 11/2008 |
| WO | WO 2008/148071 | 12/2008 |
| WO | WO 2008/148967 | 12/2008 |
| WO | WO 2008/157608 | 12/2008 |
| WO | WO 2009/003135 | 12/2008 |
| WO | WO 2009/024350 | 2/2009 |
| WO | WO 2009/024719 | 2/2009 |
| WO | WO 2009/026158 | 2/2009 |
| WO | WO 2009/028764 | 3/2009 |
| WO | WO 2009/034559 | 3/2009 |
| WO | WO 2009/073437 | 6/2009 |
| WO | WO 2010/003104 | 1/2010 |
| WO | WO 2010/003797 | 1/2010 |
| WO | WO 2010/015900 | 2/2010 |
| WO | WO 2010/026299 | 3/2010 |
| WO | WO 2010/027471 | 3/2010 |
| WO | WO 2010/028025 | 3/2010 |
| WO | WO 2010/029344 | 3/2010 |
| WO | WO 2010/038771 | 4/2010 |
| WO | WO 2010/051641 | 5/2010 |
| WO | WO 2010/052430 | 5/2010 |
| WO | WO 2010/053918 | 5/2010 |
| WO | WO 2010/061005 | 6/2010 |
| WO | WO 2011/023355 | 3/2011 |
| WO | WO 2011/072399 | 6/2011 |
| WO | WO 2011/135150 | 11/2011 |
| WO | WO 2012/008722 | 1/2012 |
| WO | WO 2012/077055 | 6/2012 |
| WO | WO 2013/015579 | 1/2013 |
| WO | WO 2013/036568 | 3/2013 |
| WO | WO 2013/067293 | 5/2013 |
| WO | WO 2013/086024 | 6/2013 |

OTHER PUBLICATIONS

Adams, "An Analysis of Clinical Studies of the Uses of Crosslinked Hyaluronan, Hylan, in the Treatment of Osteoarthritis," J Rheumatol Suppl, Aug. 1993, 39:16-8.
Aesthetic Buyers Guide, "Juvederm Raises Standards," Jan./Feb. 2007, 5 pages, www.miinews.com.
Albano et al., "Hyroxyethyl Radicals in Ethanol Hepatotoxicity," Frontiers in Bioscience, 1999, vol. 4, pp. 533-540.
Allemann et al., "Hyaluronic Acid Gel (Juvederm) Preparations in the Treatment of Facial Wrinkles and Folds," Clinical Interventions in Aging, 2008, 629-634, 3 (4).
Antunes et al., "Efficacy of Intrarectal Lidocaine Hydrochloride Gel for Pain Control in Patients Undergoing Transrectal Prostate Biopsy," Clinical Urology, 2004, 380-383, 30.
Atanassoff et al., "The Effect of Intradermal Administration of Lidocaine and Morphine on the Response to Thermal Stimulation," Anesth Analg, 1997, pp. 1340-1343.
Baumann et al., "Comparison of Smooth-Gel Hyaluronic Acid Dermal Fillers with Cross-linked Bovine Collagen: A Multicenter, Double-Masked, Randomized, Within-Subject Study," Dermatologic Surgery, 2007, vol. 33, No. 2, pp. S128-135.
Beasley et al., "Hyaluronic Acid Fillers: A Comprehensive Review," Facial Plastic Surgery, 2009, vol. 25, No. 2, pp. 86-94.
Beer, "Dermal Fillers and Combinations of Fillers for Facial Rejuvenation," Dermatologic Clin, 2009, vol. 27, No. 4, pp. 427-432.
Belda et al., "Hyaluronic Acid Combined With Mannitol to Improve Protection Against Free-Radical Endothelial Damage: Experimental Model," J Cataract Refract Surg, 2005, vol. 31, pp. 1213-1218.
Bircher et al., "Delayed-type Hypersensitivity to Subcutaneous Lidocaine With Tolerance to Articaine: Confirmation by In Vivo and In Vitro Tests," Contact Dermatitis, 1996, vol. 34, pp. 387-389.
Bluel et al., "Evaluation of Reconstituted Collagen Tape as a Model for Chemically Modified Soft Tissues," Biomat. Med. Dev. Art. Org., 1981, vol. 9, No. 1, pp. 37-46.
Boulle et al., "Lip Augmentation and Contour Correction with a Ribose Cross-linked Collagen Dermal Filler," Journal of Drugs in Dermatology, Mar. 2009, vol. 8, Issue 3, 8 pages.
Buck, "Injectable Fillers for Facial Rejuvenation: A Review," Journal of Plastic, Reconstructive & Aesthetic Surgery, 2009, vol. 62, pp. 11-18.
Calderon et al., "Type II Collagen-Hyaluronan Hydrogel—A Step Towards a Scaffold for Intervertebral Disc Tissue Engineering," European Cells and Materials, 2010, vol. 20, pp. 134-148.
Cappozi et al., "Distant Migration of Silicone Gel From a Ruptured Breast Implant," Silicone Gel Migration, 1978, vol. 62, No. 2, pp. 302-303.
Carlin et al., "Effect of Anti-Inflammatory Drugs on Xanthine Oxidase and Xanthine Oxidase Induced Depolymerization of Hyaluronic Acid," Agents and Actions, 1985, vol. 16, No. 5, pp. 377-384.
Carruthers Jean et al., "The Science and Art of Dermal Fillers for Soft-Tissue Augmentation," Journal of Drugs in Dermatology, 2009, vol. 8, No. 4, pp. 335-350.
Champion et al., "Role of Target Geometry in Phagocytosis," Proc. Nat. Acad. Sci., 2006, vol. 103, No. 13, pp. 4930-4934.
Chin et al., "Allergic Hypersensitivity to Lidocaine Hydrochloride," International Society of Tropical Dermatology, 1980, pp. 147-148.
Chvapil, "Collagen Sponge: Theory and Practice of Medical Applications," J. Biomed. Mater. Res., 1977, vol. 11, pp. 721-741.
Clark et al., "The Influence of Triamcinolone Acetonide on Joint Stiffness in the Rat," The Journal of Bone and Joint Surgery, 1971, vol. 53A, No. 7, pp. 1409-1414.
Cohen et al., "Organization and Adhesive Properties of the Hyaluronan Pericellular Coat of Chondrocytes and Epithelial Cells," Biophysical Journal, 2003, vol. 85, pp. 1996-2005.
Crosslinking Technical Handbook, Termo Scientific, Apr. 2009, pp. 1-48.
Cui et al., "The Comparison of Physicochemical Properties of Four Cross-linked Sodium Hyaluronate Gels With Different Crosslinking Agents," Advanced Materials Research, 2012, vols. 396-398, pp. 1506-1512.
Davidenko et al., "Collagen-hyaluronic acid scaffolds for adipose tissue engineering," Acta Biomaterialia, 2010, vol. 8, pp. 3957-3968.
Deland, "Intrathecal Toxicity Studies with Benzyl Alcohol," Toxicology and Applied Pharmacology, 1973, vol. 25, pp. 153-156.
Desai et al., "Molecular Weight of Heparin Using 13C Nuclear Magnetic Resonance Spectroscopy," J Pharm Sci., 1995, vol. 84, No. 2, pp. 212-215.
Eyre et al., "Collagen Cross-Links," Top Curr Chem, 2005, vol. 247, pp. 207-229.
Falcone et al., "Crosslinked Hyaluronic Acid Dermal Fillers: A Comparison of Rheological Properties," Journal of Biomedical Materials Research, 2008, vol. 87, No. 1, pp. 264-271.

(56) References Cited

OTHER PUBLICATIONS

Falcone et al., "Temporary Polysaccharide Dermal Fillers: A Model for Persistence Based on Physical Properties," Dermatologic Surgery, 2009, vol. 35, No. 8, pp. 1238-1243.
Farley et al., "Diluting Lidocaine and Mepivacaine in Balanced Salt Solution Reduces the Pain of Intradermal Injection," Regional Anesthesia, 1994, vol. 19, No. 1, pp. 48-51.
Frati et al., "Degradation of Hyaluronic Acid by Photosensitized Riboflavin In Vitro. Modulation of the Effect by Transition Metals, Radical Quenchers, and Metal Chelators," Free Radical Biology Medicine, 1996, vol. 22, No. 7, pp. 1139-1144.
Fujinaga et al., "Reproductive and Teratogenic Effects of Lidocaine in Sprague-Dawley Rats," Anesthesiology, 1986, vol. 65, pp. 626-632.
Gammaitoni et al., "Pharmacokinetics and Safety of Continuously Applied Lidocaine Patches 5%," Am J Health Syst Pharm, 2002, vol. 59, pp. 2215-2220.
Ginshicel Mh, Hydroxy Propyl Methyl Cellulose, Retrieved on Nov. 12, 2008 http://www.ginshicel.cn/MHPC.html, 2007, p. 1-3, 2 (3).
Gold, "Use of Hyaluronic Acid Fillers for the Treatment of the Aging Face," Clin. Interventions Aging, 2007, vol. 2, No. 3, pp. 369-376.
Goldberg, "Breakthroughs in US dermal fillers for facial soft-tissue augmentation," Journal of Cosmetic and Laser Therapy, 2009, vol. 11, pp. 240-247.
Gomis et al., "Effects of Different Molecular Weight Elastoviscous Hyaluronan Solutions on Articular Nociceptive Afferents," Arthritis and Rheumatism, Jan. 2004, vol. 50, No. 1, pp. 314-326.
Grafe et al., "Sensitive and Specific Photometric Determination of Mannitol," Clin Chem Lab Med, 2003, vol. 41, No. 8, pp. 1049-1055.
Grecomoro et al., "Intra-articular treatment with sodium hyaluronate in gonarthrosis: a controlled clinical trial versus placebo," Pharmatherapeutica, 1987, vol. 5, No. 2, pp. 137-141.
Grillo et al., "Thermal Reconstitution of Collagen From Solution and the Response to Its Heterologous Implantation," JSR, 1962, vol. 2, No. 1, pp. 69-82.
Hassan et al., "Effects of Adjuvants to Local Anaesthetics on Their Duration. III. Experimental Studies of Hyaluronic Acid," Acta Anaesthesiol Scand., 1985, 1 page Abstract.
Hayashibara, AA2G, Sep. 23, 2007, Retrieved on Jan. 17, 2012, http://web.archive.org/web/20070923072010/http://www.hayashibara-intl.com-/cosmetics/aa2g.html, 3 pages.
Helary et al., "Concentrated collagen hydrogels as dermal substitutes," Biomaterials, 2010, vol. 31, pp. 481-490.
Helliwell, "Use of an objective measure of articular stiffness to record changes in finger joints after intra-articular injection of corticosteroid," Annals of Rheumatic Diseases, 1997, vol. 56, pp. 71-73.
Hertzberger-Ten et al., "Intra-articular steroids in pauciarticular juvenile chronic arthritis, type 1," European Journal of Pediatrics, 1991, vol. 150, pp. 170-172.
Hetherington et al., "Potential for Patient Harm from Intrathecal Administration of Preserved Solutions," Med J Aust., 2000, 1 page abstract.
Hurst, "Adhesive Arachnoiditis and Vascular Blockage Caused by Detergents and Other Chemical Irritants: An Experimental Study," J Path. Bact., 1955, 17 pages.
Intramed (PTY) LTD, Intramed Mannitol 20% m/v Infusion, Package Insert, Jan. 1979, 2 pages.
Kablik et al., "Comparative Physical Properties of Hyaluronic Acid Dermal Fillers," Dermatology Surgery, 2009, vol. 35, pp. 302-312.
Kim et al., "Gallotannin Isolated from Euphorbia Species, 1, 2, 6-Tri-O-galloyl-b-D-allose, Decreases Nitric Oxide Production through Inhibition of Nuclear Factor-K>B and Downstream Inducible Nitric Oxide Synthase Expression in Macrophages," Jun. 2009, Biological and Pharmaceutical Bulletin, vol. 32, No. 6, pp. 1053-1056.
Klein, "Skin Filling Collagen and Other Injectables of the Skin," Fundamentals of Cosmetic Surgery, 2001, vol. 3, No. 19, pp. 491-508.
Kopp et al., "The Short-term Effect of Intra-articular Injections of Sodium Hyaluronate and Corticosteroid on Temporomandibular Joint Pain and Dysfunction," Journal of Oral and Maxillofacial Surgery, 1985, vol. 43, pp. 429-435.
Kulicke et al., "Visco-Elastic Properties of Sodium Hyaluronate Solutions," Institute for Technical and Macromolecular Chemistry, 2008, pp. 585-587.
Laeschke, "Biocompatibility of Microparticles Into Soft Tissue Fillers," Semin Cutan Med Surg, 2004, vol. 23, pp. 214-217.
Lamar et al., "Antifibrosis Effect of Novel Gels in Anterior Ciliary Sclerotomy (ACS)," The Association for Research in Vision and Ophthalmology, Inc., 2002, 1 page.
Levy et al., "Lidocaine Hypersensitivity After Subconjunctival Injection," Can J Ophthalmol, 2006, vol. 41, 204-206.
Lindvall et al., "Influence of Various Compounds on the Degradation of Hyaluronic Acid by a Myeloperoxidase System," Chemico-Biological Interactions, 1994, vol. 90, pp. 1-12.
Lupo, "Hyaluronic Acid Fillers in Facial Rejuvenation," Seminars in Cutaneous Medicine and Surgery, 2006, vol. 25, pp. 122-126.
Mackley et al., "Delayed-Type Hypersensitivity to Lidocaine," Arch Dermatol, 2003, vol. 139, pp. 343-346.
Mancinelli et al., "Intramuscular High-dose Triamcinolone Acetonide in the Treatment of Severe Chronic Asthma," West J Med, 1997, col. 167, No. 5, pp. 322-329.
Matsumoto et al., "Reducing the Discomfort of Lidocaine Administration Through pH Buffering," Journal of Vascular and Interventional Radiology, 1994, vol. 5, No. 1, pp. 171-175.
McCarty et al., "Inflammatory Reaction after Intrasynovial Injection of Microcrystalline Adrenocorticosteroid Esters," Arthritis and Rheumatism, 1964, vol. 7, No. 4, pp. 359-367.
Nadim et al., "Improvement of polyphenol properties upon glucosylation in a UV-induced skin cell ageing model," International Journal of Cosmetic Science, Sep. 2014, vol. 36, No. 6, pp. 579-587.
Gallic Acid, National Center for Biotechnology Information, PubChem Compound Database, CID=370, 2018, https://pubchem.ncbi.nim.nih.gov/compound/370, 1 page.
Caffeic Acid, National Center for Biotechnology Information, PubChem Compound Database, CID=689043, 2018, https://pubchem.ncbi.nim.nih.gov/compound/689043, 1 page.
Orvisky et al., "High-molecular-weight Hyaluronan—a Valuable Tool in Testing the Antioxidative Activity of Amphiphilic Drugs Stobadine and Vinpocetine," Journal of Pharm. Biomed. Anal., 1997, vol. 16, pp. 419-424.
Osmitrol (generic name Mannitol), Official FDA Information, side effects and uses, http://www.drugs.com/pro/osmitrol.html, 2010, 10 Pages.
Park et al., "In vitro evaluation of conjugated Hyaluronic acid with Ascorbic Acid," Journal of Bone and Joint Surgery, British vol. 92-B, 2010, 1 page abstract.
Park et al., "Biological Characterization of EDC-Crosslinked Collagen-Hyaluronic Acid Matrix in Dermal Tissue Restoration," Biomaterials, 2003, vol. 24, pp. 1631-1641.
Park et al., "Characterization of Porous Collagen/Hyaluronic Acid Scaffold Modified by 1-Ethyl-3-(3-Dimethylaminopropyl)Carbodiimide Cross-Linking," Biomaterials, 2002, vol. 23, pp. 1205-1212.
Powell, "Stability of Lidocaine in Aqueous Solution: Effect of Temperature, pH, Buffer, and Metal Ions on Amide Hydrolysis," Pharmaceutical Research, 1987, vol. 4, No. 1, pp. 42-45.
Prestwich, "Evaluating Drug Efficacy and Toxicology in Three Dimensions: Using Synthetic Extracellular Matrices in Drug Discovery," Accounts of Chemical Research, Jan. 2008, vol. 41, No. 1, pp. 139-148.
Rehakova et al., "Properties of Collagen and Hyaluronic Acid Composite Materials and Their Modification by Chemical Crosslinking," Journal of Biomedical Materials Research, 1996, vol. 30, pp. 369-372.
Remington's Pharmaceutical Sciences, 1980, 16th Edition, Mack Publishing Company, Easton, Pennsylvania, 10 pages.
Rosenblatt et al., "Chain Rigidity and Diffusional Release in Biopolymer Gels," Controlled Release Society, 1993, vol. 20, pp. 264-265.
Rosenblatt et al., "The Effect of Collagen Fiber Size Distribution on the Release Rate of Proteins From Collagen Matrices by Diffusion," J Controlled Release, 1989, vol. 9, pp. 195-203.

(56) References Cited

OTHER PUBLICATIONS

Sannino et al., "Crosslinking of Cellulose Derivatives and Hyaluronic Acid With Water-Soluble Carbodiimide," Polymer, 2005, vol. 46, pp. 11206-11212.
Sculptra Product Information, Dermik Laboratories, Jun. 2004, 12 pages.
Segura et al., "Crosslinked Hyaluronic Acid Hydrogels: A Strategy to Functionalize and Pattern," Biomaterials, 2005, vol. 26, No. 4, pp. 359-371.
Selvi et al., "Arthritis Induced by Corticosteroid Crystals," The Journal of Rheumatology, 2004, vol. 31, No. 3, pp. 622.
Shu et al, "Synthesis and evaluation of injectable, in situ crosslinkable synthetic extracellular matrices for tissue engineering," Journal of Biomedical Materials Research, 2006, vol. 79A, pp. 902-912.
Silver et al., "Physical Properties of Hyaluronic Acid and Hydroxypropylmethylcellulose in Solution: Evaluation of Coating Ability," Journal of Applied Biomaterials, 1994, vol. 5, pp. 89-98.
Skardal et al., "Bioprinting Vessel-Like Constructs Using Hyaluronan Hydrogels Crosslinked With Tetrahedral Polyethylene Glycol Tetracrylates," Biomaterials, 2010, vol. 31, pp. 6173-6181.
Smith et al., "Five Percent Lidocaine Cream Applied Simultaneously to the Skin and Mucosa of the Lips Creates Excellent Anesthesia for Filler Injections," Dermatol Surg, 2005, vol. 31, pp. 1635-1637.
Tezel et al., "The science of hyaluronic acid dermal fillers," Journal of Cosmetic and Laser Therapy, 2008, vol. 10, pp. 35-42.
Tomihata et al., "Crosslinking of Hyaluronic Acid with Water-Soluable Carbodiimide," J Biomed Mater Res, Feb. 1997, vol. 37, No. 2, pp. 243-251.
Visiol, TRB Chemedica Ophthalmic Line, Product Info, May 2014, p. 1-2, Geneva, CH.
Visiol, Viscoelstic Gel for Use in Ocular Surgery, http://www.trbchemedica.com/index.php/option=com_content&tas, 2010, 1 Page.
Wahl, "European Evaluation of a New Hyaluronic Acid Filler Incorporating Lidocaine," Journal of Cosmetic Dermatology, 2008, vol. 7, pp. 298-303.
Wang et al., "Development of hyaluronic acid-based scaffolds for brain tissue engineering," Acta Biomaterialia, 2009, pp. 2371-2384.
Waraszkiewicz et al., "Stability-Indicating High-Performance Liquid Chromatographic Analysis of Lidocaine Hydrochloride and Lidocaine Hydrochloride with Epinephrine Injectable Solutions," Journal of Pharmaceutical Sciences, 1981, vol. 70, No. 11, pp. 1215-1218.
Weidmann, "New Hyaluronic Acid Filler for Subdermal and Long-lasting Volume Restoration of the Face," European Dermatology, 2009, pp. 65-68.
Xia et al., "Comparison of Effects of Lidocaine Hydrochloride, Buffered Lidocaine, Diphenhydramine, and Normal Saline After Intradermal Injection," Journal of Clinical Anesthesia, 2002, vol. 14, pp. 339-343.
Yeom et al., "Effect of Cross-Linking Reagents for Hyaluronic Acid Hydrogel Dermal Fillers on Tissue Augmentation and Regeneration," Bioconjugate Chemistry, 2010, vol. 21, pp. 240-247.
Yui et al., "Inflammation Responsive Degradation of Crosslinked Hyaluronic Acid Gels," Journal of Controlled Release, 1992, vol. 26, pp. 105-116.
Yui et al., "Photo-Responsive Degradation of Heterogeneous Hydrogels Comprising Crosslinked Hyaluronic Acid and Lipid Microspheres for Temporal Drug Delivery," Journal of Controlled Release, 1993, vol. 26, pp. 141-145.
Yun et al., "Hyaluronan Microspheres for Sustained Gene Delivery and Site-Specific Targeting," Biomaterials, 2004, vol. 25, pp. 147-157.
Zheng et al., "In situ crosslinkable hyaluronan hydrogels for tissue engineering," Biomaterials, 2004, vol. 25, pp. 1339-1348.
Zulian et al., "Triamcinolone acetonide and hexacetonide intra-articular treatment of symmetrical joints in juvenile idiopathic arthritis: a double-blind trial," Rheumatology, Oct. 2004, vol. 43, No. 10, pp. 1288-1291.
Lim et al., "Regioselectivity of glucosylation of caffeic acid by a UDP-glycose: glucosyltransferase is maintained in planta," Biochem J. 2003, vol. 373, No. 3, pp. 987-992.

* cited by examiner

STABLE HYDROGEL COMPOSITIONS INCLUDING ADDITIVES

CROSS REFERENCE TO RELATED APPLICATIONS

This application is a national phase application under 35 U.S.C. § 371 of PCT Application Serial No. PCT/IB2014/001959, filed Sep. 30, 2014, the entire disclosure of this application being incorporated herein by this specific reference.

BACKGROUND

Skin aging is a progressive phenomenon that occurs over time and can be affected by lifestyle factors, such as alcohol consumption, tobacco, and sun exposure. Aging of the facial skin can be characterized by atrophy, slackening, and fattening. Atrophy corresponds to a massive reduction of the thickness of skin tissue. Slackening of the subcutaneous tissues leads to an excess of skin and ptosis and leads to the appearance of drooping cheeks and eyelids. Fattening refers to an increase in excess weight by swelling of the bottom of the face and neck. These changes are typically associated with dryness, loss of elasticity, and rough texture.

Hyaluronan, also known as hyaluronic acid ("HA"), is a non-sulfated glycosaminoglycan that is distributed widely throughout the human body in connective, epithelial, and neural tissues. Hyaluronan is abundant in the different layers of the skin, where it has multiple functions such as, e.g., to ensure good hydration, to assist in the organization of the extracellular matrix, to act as a filler material; and to participate in tissue repair mechanisms. However, with age, the quantity of hyaluronan, collagen, elastin, and other matrix polymers present in the skin decreases. For example, repeated exposed to ultra violet light, e.g., from the sun, causes dermal cells to both decrease their production of hyaluronan as well as increase the rate of its degradation. This hyaluronan loss results in various skin conditions such as, e.g., imperfects, defects, diseases and/or disorders, and the like. For instance, there is a strong correlation between the water content in the skin and levels of hyaluronan in the dermal tissue. As skin ages, the amount and quality of hyaluronan in the skin is reduced. These changes lead to drying and wrinkling of the skin.

Dermal fillers are useful in treating soft tissue condition and in other skin therapies because the fillers can replace lost endogenous matrix polymers, or enhance/facilitate the function of existing matrix polymers, in order to treat these skin conditions. In the past, such compositions have been used in cosmetic applications to fill wrinkles, lines, folds, scars, and to enhance dermal tissue, such as, e.g., to plump thin lips, or fill-in sunken eyes or shallow cheeks. One common matrix polymer used in dermal filler compositions is hyaluronan. Because hyaluronan is natural to the human body, it is a generally well tolerated and a fairly low risk treatment for a wide variety of skin conditions.

Originally, compositions comprising hyaluronan where made from naturally occurring polymers, which exist in an uncrosslinked state. Although exhibiting excellent biocompatibility and affinity for water molecules, naturally occurring hyaluronan exhibits poor biomechanical properties as a dermal filler. One primary reason is that because this polymer is uncrosslinked, it is highly soluble and, as such, is cleared rapidly when administered into a skin region. This in vivo clearance is primarily achieved by rapid degradation of the polymers, principally enzymatic degradation via hyaluronidase and chemical degradation via free radicals. Thus, while still in commercial use, compositions comprising uncrosslinked hyaluronan polymers tend to degrade within a few days after administration and thus require fairly frequent reinjection to maintain their skin improving effect.

To minimize the effect of these in vivo degradation pathways, matrix polymers are crosslinked to one another to form a stabilized hydrogel. Because hydrogels comprising crosslinked matrix polymers are a more solid substance, dermal fillers comprising such hydrogels remain in place at the implant site longer. In addition, these hydrogels are more suitable as a dermal filler because it is more solid nature improves the mechanical properties of the filler, allowing the filler to better lift and fill a skin region. Hyaluronan polymers are typically crosslinked with a crosslinking agent to form covalent bonds between hyaluronan polymers. Such crosslinked polymers form a less water soluble hydrogel network that is more resistant to degradation, and thus requires less frequent reinjection, than the non-crosslinked hyaluronan compositions.

Current dermal fillers can be associated with a variety of side effects. For example, administration of a dermal filler to an individual is typically performed using a syringe or needle. Such administration could result in one or more unwanted side-effects, such as, e.g., pain and discomfort to the individual, bleeding in and under the site of administration, and itching, inflammation and irritation in the vicinity of the administration site during and after the administration of the dermal filler. The dermal fillers disclosed in the present specification address these and other unwanted side-effects by providing hydrogel compositions comprising agents that reduce, step, or prevent one or more of these side-effects.

Additionally, a dermal filler formulation must be capable of withstanding sterilization which is a strict requirement before the product can be sold (the product must be sterile). Sterilization can be carried out by steam sterilization, filtration, microfiltration, gamma radiation, ETO light or by a combination of these methods. It is known that a dermal filler can be steam sterilized (autoclaved) without substantial degradation of physical properties, but when a dermal filler formulation contains an additional labile ingredient (such as an antioxidant, anti-itch agent, an anti-cellulite agent, an anti-scarring agent, an anti-inflammatory agent, an anesthetic agent, an anti-irritant agent, a vasoconstrictor, a vasodilator, an anti-hemorrhagic agent like a hemostatic agent or anti-fibrinolytic agent, a desquamating agent, a tensioning agent, an anti-acne agent, a pigmentation agent, an anti-pigmentation agent, or a moisturizing agent) the entire dermal filler formulation or at least the additional (heat labile) agent is traditionally sterilized by a non-heat treatment such as by a filtration sterilization method. Thus, a known dermal filler product (REVITACARE® Bio-Revitalisation, REVITACARE® Laboratory, Saint-Ouen-l'Aumône, France) is sold in two separate vials or containers, one vial containing the HA (which is autoclave sterilized)) and the second vial containing any additional ingredients (the second vial contents are sterilized by filtration). Another known dermal filler product NCTF® 135HA (Laboratoires Filorga, Paris, France) is sold in a single container holding both hyaluronan and any additional ingredients, all having been sterilized by microfiltration. The dermal fillers disclosed in the present specification addresses this issue by developing dermal fillers that are entirely sterilized by a heat treatment, i.e., in some embodiments of this invention, none of the components are sterilized solely using a non-heat treatment such as, e.g., filtration.

SUMMARY

The present specification provides novel dermal fillers useful for treating skin conditions that remain stable after a heat treatment used to sterilize the compositions. One aspect of the disclosed dermal fillers, and a significant distinction over known dermal fillers, is that dermal fillers disclosed herein are prepared by: (1) mixing glycosaminoglycan polymers and the additional agents(s) disclosed herein, and then; (2) heat treating the dermal filler composition to at least 100° C. (no filtration sterilization of any component); (3) where such treatment maintains the desired properties of the hydrogel compositions. In some embodiments, the disclosed hydrogel compositions do not exhibit any significant degradation as shown by pre and post autoclaved testing. In some embodiments, the disclosed hydrogel compositions are substantially heat stable as determined by the retention of one or more of the following characteristics after sterilization: clarity (transparency and translucency), homogeneousness, extrusion force, cohesiveness, hyaluronan concentration, agent(s) concentration, osmolarity, pH, or other rheological characteristics desired by the hydrogel before the heat treatment.

The hydrogel compositions disclosed herein can also exhibit greater stability than a hydrogel composition without the additional constituent. Additionally, the additional ingredient can be hydrophilic and provides protection to the glycosaminoglycan polymers from degradation during steam sterilization and/or after administration of the dermal filler formulation to a patient. Without wishing to be bound by theory, the incorporation of an additional ingredient in the dermal filler formulation may inhibit free-radical scavenging at the injection/implant site, thereby prolonging dermal filler duration after patient administration.

Thus, aspect of the present specification provide a hydrogel composition comprising a glycosaminoglycan polymer and one or more antioxidant agents.

Some aspects of the present specification provide a method of preparing a hydrogel composition disclosed herein, the method comprising (a) mixing the glycosaminoglycan polymer and the at least one agent; and (b) heat treating the mixture, wherein the heat treatment maintains the desired hydrogel properties disclosed herein.

Some aspects of the present specification provide a method of treating a skin condition in an individual in need thereof, the method comprising the steps of administering, for example, by subdermal injection, a hydrogel composition disclosed herein into a dermal region of the individual, wherein the administration improves the skin condition. Skin conditions treated by the disclosed compositions include, without limitation, augmentations, reconstructions, diseases, disorders, defects, or imperfections of a body part, region or area. In one aspect, a skin condition treated by the disclosed compositions include, without limitation, a facial augmentation, a facial reconstruction, a facial disease, a facial disorder, a facial defect, or a facial imperfection. In one aspect, a skin condition treated by the disclosed compositions include, without limitation, skin dehydration, a lack of skin elasticity, skin roughness, a lack of skin tautness, a skin stretch line or mark, skin paleness, a dermal divot, a sunken cheek, a thin lip, a retro-orbital defect, a facial fold, or a wrinkle.

In some embodiments a hydrogel composition comprising a hyaluronic acid-based polymer and at least one antioxidant is provided, wherein the hydrogel composition is sterilized by heat treatment and/or pressure treatment, for example, by autoclaving, for example, is sterilized in a process comprising a heat treatment of at least 100° C. Advantageously, the heat sterilized composition is substantially stable at room temperature for up to at least about 3 months, for example, at least about 12 months, at least about 24 months, or at least about 36 months.

In some embodiments, the antioxidant agent can be a phenolic molecule. Non-limiting examples of phenolic molecules suitable in embodiments of the present invention include; caffeic acid, catechin, epigallocatechin gallate, kaempferol, quercetin, and luteolin. In some embodiments, the antioxidant agent it a glucosidic derivative of a phenolic agent.

In some embodiments, the antioxidant is water-soluble, and is preferably the glucosylated derivative of a non water-soluble antioxidant. For example, the antioxidant one of a glucosylated caffeic acid, a glucosylated epicatechin gallate or a glucosylated epigallocatechin gallate.

In some embodiments, the phenolic agent is directly incorporated into a hyaluronic acid based gel, for example, a crosslinked hyaluronic acid based gel. In these embodiments, such direct incorporation of antioxidizing agents increases the resistance of the gel composition to oxidative stress such as free radicals. Typically, in a free radical degradation test where gel compositions are exposed to hydrogen peroxide and the complex viscosity or elastic modulus of the compositions are followed by oscillation rheology, the incorporation of antioxidant agents increases the time it takes until the visco-elastic properties drop to a certain level, or drop by a given percentage. Typically, $T_{30}$, the time it takes to lose 70% of the initial elastic modulus or complex viscosity is used to rank formulations. In some embodiments, the HA composition comprising crosslinked HA and the antioxidant provides at least about a 25% increase for $T_{30}$, preferably at least about a 50% increase for $T_{30}$, and even more preferably at least about a 100% increase for $T_{30}$.

In some embodiments, the free radical scavenger properties of the gel obtained according to the present disclosure showed an improvement in the stability of the formulation when compared with a gel without the additive.

In some embodiments, the composition further comprises an anesthetic agent, for example, lidocaine or a similar agent, present in an amount of about 0.1% (w/w) to about 1.0% (w/w) of the total composition. In some embodiments, lidocaine is present in an amount of about 0.3% w/w. In some embodiments, the composition further comprises an antioxidant agent, for example, mannitol present in an amount of about 0.01% (w/w) to about 5% (w/w) of the total composition. In some embodiments, the hyaluronic acid-based polymer is present at a concentration of about 5 mg/g to about 40 mg/g, and comprises a low molecular weight hyaluronan polymer having a mean molecular weight greater than 300,000 Da and less than about 800,000 Da, for example, a mean molecular weight greater than 2,000,000 Da and less than about 5,000,000 Da. In some embodiments, the hyaluronic acid-based polymer comprises both high molecular weight hyaluronan and low molecular weight hyaluronan, wherein the high molecular weight hyaluronan has a molecular weight greater than 2,000,000 Da and wherein the low molecular weight hyaluronan has a molecular weight of less than 1,000,000 Da.

DETAILED DESCRIPTION

Figure 1:
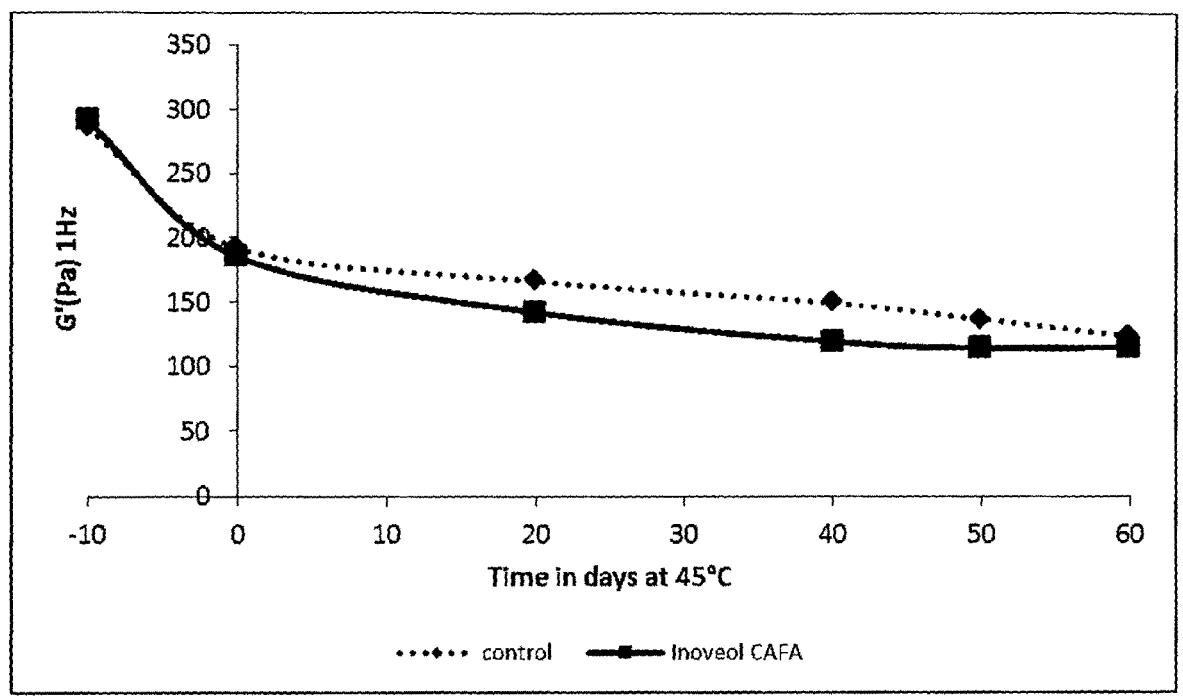
FIG. 1 is a graph illustrating experimental data obtained that demonstrates the effect of an accelerated aging/accelerated degradation at 45° C. for 60 days on the elastic modulus G' of the same gel with and without Inoveol® CAFA at 0.5% (w/w).

Aspects of the present specification provide, in part, a hydrogel composition comprising a glycosaminoglycan polymer. The hydrogel composition disclosed herein can further comprise two or more different glycosaminoglycan polymers. As used herein, the term "glycosaminoglycan" is synonymous with "GAG" and "mucopolysaccharide" and refers to long unbranched polysaccharides consisting of a repeating disaccharide units. The repeating unit consists of a hexose (six-carbon sugar) or a hexuronic acid, linked to a hexosamine (six-carbon sugar containing nitrogen) and pharmaceutically acceptable salts thereof. Members of the GAG family vary in the type of hexosamine, hexose or hexuronic acid unit they contain, such as, e.g., glucuronic acid, iduronic acid, galactose, galactosamine, glucosamine) and may also vary in the geometry of the glycosidic linkage. Any glycosaminoglycan polymer is useful in the hydrogel compositions disclosed herein with the proviso that the glycosaminoglycan polymer improves a condition of the skin. Non-limiting examples of glycosaminoglycans include chondroitin sulfate, dermatan sulfate, keratan sulfate, hyaluronan. Non-limiting examples of an acceptable salt of a glycosaminoglycan includes sodium salts, potassium salts, magnesium salts, calcium salts, and combinations thereof. GAGs useful in the hydrogel compositions and methods disclosed herein include those commercially available, such as, e.g., hyaluronan-based dermal fillers JUVEDERM®, JUVEDERM® 30, JUVEDERM® Ultra, JUVEDERM® Ultra Plus, JUVEDERM® Ultra XC, and JUVEDERM® Ultra Plus XC (Allergan Inc, Irvine, Calif.). Table 1 lists representative GAGs.

TABLE 1

Examples of GAGs

| Name | Hexuronic acid/Hexose | Hexosamine | Glycosidic linkage geometry | Unique features |
|---|---|---|---|---|
| Chondroitin sulfate | GlcUA or GlcUA(2S) | GalNAc or GalNAc(4S) or GalNAc(6S) or GalNAc(4S,6S) | -4GlcUAβ1-3GalNAcβ1- | Most prevalent GAG |
| Dermatan sulfate | GlcUA or IdoUA or IdoUA(2S) | GalNAc or GalNAc(4S) or GalNAc(6S) or GalNAc(4S,6S) | -4IdoUAβ1-3GalNAcβ1- | Distinguished from chondroitin sulfate by the presence of iduronic acid, although some hexuronic acid monosaccharides may be glucuronic acid. |
| Keratan sulfate | Gal or Gal(6S) | GlcNAc or GlcNAc(6S) | -3Gal(6S)β1-4GlcNAc(6S)β1- | Keratan sulfate type II may be fucosylated. |
| Heparin | GlcUA or IdoUA(2S) | GlcNAc or GlcNS or GlcNAc(6S) or GlcNS(6S) | -4IdoUA(2S)α1-4GlcNS(6S)α1- | Highest negative charge density of any known biological molecule |
| Heparan sulfate | GlcUA or IdoUA or IdoUA(2S) | GlcNAc or GlcNS or GlcNAc(6S) or GlcNS(6S) | -4GlcUAβ1-4GlcNAcα1- | Highly similar in structure to heparin, however heparan sulfates disaccharide units are organised into distinct sulfated and non-sulfated domains. |

TABLE 1-continued

Examples of GAGs

| Name | Hexuronic acid/Hexose | Hexosamine | Glycosidic linkage geometry | Unique features |
|---|---|---|---|---|
| Hyaluronan | GlcUA | GlcNAc | -4GlcUAβ1-3GlcNAcβ1- | The only GAG that is exclusively non-sulfated |

GlcUA = β-D-glucuronic acid
GlcUA(2S) = 2-O-sulfo-β-D-glucuronic acid
IdoUA = α-L-iduronic acid
IdoUA(2S) = 2-O-sulfo-α-L-iduronic acid
Gal = β-D-galactose
Gal(6S) = 6-O-sulfo-β-D-galactose
GalNAc = β-D-N-acetylgalactosamine
GalNAc(4S) = β-D-N-acetylgalactosamine-4-O-sulfate
GalNAc(6S) = β-D-N-acetylgalactosamine-6-O-sulfate
GalNAc(4S,6S) = β-D-N-acetylgalactosamine-4-O, 6-O-sulfate
GlcNAc = α-D-N-acetylglucosamine
GlcNS = α-D-N-sulfoglucosamine
GlcNS(6S) = α-D-N-sulfoglucosamine-6-O-sulfate Aspects of the present specification provide, in part, a hydrogel composition comprising a chondroitin sulfate polymer. As used herein, the term "chondroitin sulfate polymer" refers to an unbranched, sulfated polymer of variable length comprising disaccharides of two alternating monosaccharides of D-glucuronic acid (GlcA) and N-acetyl-D-galactosamine (GalNAc) and pharmaceutically acceptable salts thereof. A chondroitin sulfate polymer may also include D-glucuronic acid residues that are epimerized into L-iduronic acid (IdoA), in which case the resulting disaccharide is referred to as dermatan sulfate. A chondroitin sulfate polymer can have a chain of over 100 individual sugars, each of which can be sulfated in variable positions and quantities. Chondroitin sulfate polymers are an important structural component of cartilage and provide much of its resistance to compression. Any chondroitin sulfate polymer is useful in the compositions disclosed herein with the proviso that the chondroitin sulfate polymer improves a condition of the skin. Non-limiting examples of pharmaceutically acceptable salts of chondroitin sulfate include sodium chondroitin sulfate, potassium chondroitin sulfate, magnesium chondroitin sulfate, calcium chondroitin sulfate, and combinations thereof.

Aspects of the present specification provide, in part, a hydrogel composition comprising a keratan sulfate polymer. As used herein, the term "keratan sulfate polymer" refers to a polymer of variable length comprising disaccharide units, which themselves include β-D-galactose and N-acetyl-D-galactosamine (GalNAc) and pharmaceutically acceptable salts thereof. Disaccharides within the repeating region of keratan sulfate may be fucosylated and N-Acetylneuraminic acid caps the end of the chains. Any keratan sulfate polymer is useful in the compositions disclosed herein with the proviso that the keratan sulfate polymer improves a condition of the skin. Non-limiting examples of pharmaceutically acceptable salts of keratan sulfate include sodium keratan sulfate, potassium keratan sulfate, magnesium keratan sulfate, calcium keratan sulfate, and combinations thereof.

Aspects of the present specification provide, in part, a hydrogel composition comprising a hyaluronan polymer. As used herein, the term "hyaluronic acid polymer" is synonymous with "HA polymer", "hyaluronic acid polymer", and "hyaluronate polymer" refers to an anionic, non-sulfated glycosaminoglycan polymer comprising disaccharide units, which themselves include D-glucuronic acid and D-N-acetylglucosamine monomers, linked together via alternating β-1,4 and β-1,3 glycosidic bonds and pharmaceutically acceptable salts thereof. Hyaluronan polymers can be purified from animal and non-animal sources. Polymers of hyaluronan can range in size from about 5,000 Da to about 20,000,000 Da. Any hyaluronan polymer is useful in the compositions disclosed herein with the proviso that the hyaluronan improves a condition of the skin. Non-limiting examples of pharmaceutically acceptable salts of hyaluronan include sodium hyaluronan, potassium hyaluronan, magnesium hyaluronan, calcium hyaluronan, and combinations thereof.

Aspects of the present specification provide, in part, a hydrogel composition comprising a crosslinked glycosaminoglycan polymer. As used herein, the term "crosslinked" refers to the intermolecular bonds joining the individual polymer molecules, or monomer chains, into a more stable structure like a gel. As such, a crosslinked glycosaminoglycan polymer has at least one intermolecular bond joining at least one individual polymer molecule to another one. The crosslinking of glycosaminoglycan polymers typically result in the formation of a hydrogel. Such hydrogels have high viscosity and require considerable force to extrude through a fine needle.

Glycosaminoglycan polymers disclosed herein may be crosslinked using dialdehydes and disulfides crosslinking agents including, without limitation, multifunctional PEG-based crosslinking agents, divinyl sulfones, diglycidyl ethers, and bis-epoxides, biscarbodiimide. Non-limiting examples of hyaluronan crosslinking agents include multifunctional PEG-based crosslinking agents like pentaerythritol tetraglycidyl ether (PETGE), divinyl sulfone (DVS), 1,4-butanediol diglycidyl ether (BDDE), 1,2-bis(2,3-epoxypropoxy)ethylene (EGDGE), 1,2,7,8-diepoxyoctane (DEO), (phenylenebis-(ethyl)-carbodiimide and 1,6 hexamethylenebis (ethylcarbodiimide), adipic dihydrazide (ADH), bis (sulfosuccinimidyl)suberate (BS), hexamethylenediamine (HMDA), 1-(2,3-epoxypropyl)-2,3-epoxycyclohexane, or combinations thereof.

In accordance with the present specification, "%" in a formulation is defined as weight by weight (i.e., w/w) percentage. As an example: 1% (w/w) means a concentration of 10 mg/g.

In one aspect, a hydrogel composition is provided comprising a crosslinked glycosaminoglycan polymer. For example, the composition may comprise a crosslinked chondroitin sulfate polymer, a crosslinked dermatan sulfate polymer, a crosslinked keratan sulfate polymer, a crosslinked heparan polymer, a crosslinked heparan sulfate polymer, or a crosslinked hyaluronan polymer. The crosslinked glycosaminoglycan may be present, e.g., about 1% by weight, about 2% by weight, about 3% by weight, about 4% by weight, about 5% by weight, about 6% by weight, about 7% by weight, about 8% by weight, or about 9%, or about 10% by weight, of the total glycosaminoglycan present in the composition. In yet other aspects of this embodiment, a composition comprises a crosslinked glycosaminoglycan where the crosslinked glycosaminoglycan represents, e.g., at most 1% by weight, at most 2% by weight, at most 3% by weight, at most 4% by weight, at most 5% by weight, at most 6% by weight, at most 7% by weight, at most 8% by weight, at most 9% by weight, or at most 10% by weight, of the total glycosaminoglycan present in the composition. In still other aspects of this embodiment, a composition comprises a crosslinked glycosaminoglycan where the crosslinked glycosaminoglycan represents, e.g., about 0% to about 20% by weight, about 1% to about 17% by weight, about 3% to about 15% by weight, or about 5% to about 10% by weight, for example, about 11% by weight, about 15% by weight or about 17% by weight, of the total glycosaminoglycan present in the composition.

The crosslinked glycosaminoglycan may be present in the composition at a concentration of, e.g., about 2 mg/g, about 3 mg/g, about 4 mg/g, about 5 mg/g, about 6 mg/g, about 7 mg/g, about 8 mg/g, about 9 mg/g, about 10 mg/g, about 11 mg/g, about 12 mg/g, about 13 mg/g, about 13.5 mg/g, about 14 mg/g, about 15 mg/g, about 16 mg/g, about 17 mg/g, about 18 mg/g, about 19 mg/g, or about 20 mg/g, or greater, for example, up to about 40 mg/g. In other aspects of this embodiment, a composition comprises a crosslinked glycosaminoglycan where the crosslinked glycosaminoglycan is present at a concentration of, e.g., at least 1 mg/g, at least 2 mg/g, at least 3 mg/g, at least 4 mg/g, at least 5 mg/g, at least 10 mg/g, at least 15 mg/g, at least 20 mg/g, or at least 25 mg/g, or about 40 mg/g. In yet other aspects of this embodiment, a composition comprises a crosslinked glycosaminoglycan where the crosslinked glycosaminoglycan is present at a concentration of, e.g., at most 1 mg/g, at most 2 mg/g, at most 3 mg/g, at most 4 mg/g, at. most 5 mg/g, at most 10 mg/g, at most 45 mg/g, at most 20 mg/g, at most 25 mg/g, or at most 40 mg/g. In still other aspects of this embodiment, a composition comprises a crosslinked glycosaminoglycan where the crosslinked glycosaminoglycan is present at a concentration of, e.g., about 7.5 mg/g to about 19.5 mg/g, about 8.5 mg/g to about 18.5 mg/g, about 9.5 mg/g to about 17.5 mg/g, about 10.5 mg/g to about 16.5 mg/g, about 11.5 mg/g to about 15.5 mg/g, or about 12.5 mg/g to about 14.5 mg/g, up to about 40 mg/g.

Aspects of the present specification provide, in part, a hydrogel composition comprising hyaluronan polymers of low molecular weight, hyaluronan polymers of high molecular weight, or hyaluronan polymers of both low and high molecular weight. As used herein, the term "high molecular weight" when referring to "hyaluronan" refers to hyaluronan polymers having a mean molecular weight of 1,000,000 Da or greater. Non-limiting examples of a high molecular weight hyaluronan polymers include hyaluronan polymers about 1,500,000 Da, about 2,000,000 Da, about 2,500,000 Da, about 3,000,000 Da, about 3,500,000 Da, about 4,000,000 Da, about 4,500,000 Da, and about 5,000,000 Da. As used herein, the term "low molecular weight" when referring to "hyaluronan" refers to hyaluronan polymers having a mean molecular weight of less than 1,000,000 Da. Non-limiting examples of a low molecular weight hyaluronan polymers include hyaluronan polymers of about 100,000 Da, about 200,000 Da, about 300,000 Da, about 400,000 Da, about 500,000 Da, about 600,000 Da, about 700,000 Da, of about 800,000 Da, and about 900,000 Da.

In yet another embodiment, a composition comprises crosslinked hyaluronan polymers where the crosslinked hyaluronan polymers comprise a combination of both high molecular weight hyaluronan polymers and low molecular weight hyaluronan polymers, in various ratios. In aspects of this embodiment, a composition comprises crosslinked hyaluronan polymers where the crosslinked hyaluronan polymers comprise a combination of both high molecular weight hyaluronan polymers and low molecular weight hyaluronan polymers in a ratio of about 20:1, about 15:1, about 10:1, about 5:1, about 1:1, about 1:5 about 1:10, about 1:15, or about 1:20.

Aspects of the present specification provide, in part, a hydrogel composition comprising a crosslinked glycosaminoglycan polymer having a degree of crosslinking. As used herein, the term "degree of crosslinking" refers to the percentage of glycosaminoglycan polymer monomeric units, such as, e.g., the disaccharide monomer units of hyaluronan that are bound to a cross-linking agent. The degree of crosslinking is expressed as the percent weight ratio of the crosslinking agent to glycosaminoglycan.

Aspects of the present specification provide, in part, a hydrogel composition comprising an uncrosslinked glycosaminoglycan polymer. As used herein, the term "uncrosslinked" refers to a lack of intermolecular covalent bonds joining the individual glycosaminoglycan polymer molecules, or monomer chains. As such, an uncrosslinked glycosaminoglycan polymer is not linked to any other glycosaminoglycan polymer by an intermolecular bond. In aspects of this embodiment, a composition comprises an uncrosslinked chondroitin sulfate polymer, an uncrosslinked dermatan sulfate polymer, an uncrosslinked keratan sulfate polymer, an uncrosslinked heparan polymer, an uncrosslinked heparan sulfate polymer, or an uncrosslinked hyaluronan polymer. Uncrosslinked glycosaminoglycan polymers are water soluble and generally remain fluid in: nature. As such, uncross-linked glycosaminoglycan polymers are often mixed with a glycosaminoglycan polymer-based hydrogel composition as a lubricant to facilitate the extrusion process of the composition through a fine needle.

In an embodiment, a composition comprises an uncrosslinked glycosaminoglycan polymer where the uncrosslinked glycosaminoglycan polymer is present in an amount sufficient to improve a skin condition as disclosed herein. In aspects of this embodiment, a composition comprises an uncrosslinked glycosaminoglycan where the uncrosslinked glycosaminoglycan is present at a concentration of, e.g., about 2 mg/g, about 3 mg/g, about 4 mg/g, about 5 mg/g, about 6 mg/g, about 7 mg/g, about 8 mg/g, about 9 mg/g, about 10 mg/g, about 11 mg/g, about 12 mg/g, about 13 mg/g, about 13.5 mg/g, about 14 mg/g, about 15 mg/g, about 16 mg/g, about 17 mg/g, about 18 mg/g, about 19 mg/g, about 20 mg/g, about 40 mg/g, or about 60 mg/g. In other aspects of this embodiment, a composition comprises an uncrosslinked glycosaminoglycan where the uncrosslinked glycosaminoglycan is present at a concentration of, e.g., at least 1 mg/g, at least 2 mg/g, at least 3 mg/g, at least 4 mg/g, at least 5 mg/g, at least 10 mg/g, at least 15 mg/g, at least 20 mg/g, at least 25 mg/g at least 35 mg/g, or at least 40 mg/g. In yet other aspects of this embodiment, a composition comprises an uncrosslinked glycosaminoglycan where the uncrosslinked glycosaminoglycan is present at a concentration of, e.g., at most 1 mg/g, at most 2 mg/g, at most 3 mg/g, at most 4 mg/g, at most 5 mg/g, at most 10 mg/g, at most 15 mg/g, at most 20 mg/g, or at most 25 mg/g. In still other aspects of this embodiment, a composition comprises an uncrosslinked glycosaminoglycan where the uncrosslinked glycosaminoglycan is present at a concentration of, e.g., about 1 mg/g to about 60 mg/g, about 10 mg/g to about 40 mg/g, about 7.5 mg/g to about 19.5 mg/g, about 8.5 mg/g to about 18.5 mg/g, about 9.5 mg/g to about 17.5 mg/g, about 10.5 mg/g to about 16.5 mg/g, about 11.5 mg/g to about 15.5 mg/g, or about 12.5 mg/g to about 14.5 mg/g.

In an embodiment, a composition comprises uncrosslinked hyaluronan polymers of low molecular weight. In aspects of this embodiment, a composition comprises a uncrosslinked hyaluronan having a mean molecular weight of, e.g., about 100,000 Da, about 200,000 Da, about 300,000 Da, about 400,000 Da, about 500,000 Da, about 600,000 Da, about 700,000 Da, about 800,000 Da, or about 900,000 Da. In yet other aspects of this embodiment, a composition comprises uncrosslinked hyaluronan polymers having a mean molecular weight of, e.g., at most 100,000 Da, at most 200,000 Da, at most 300,000 Da, at most 400,000 Da, at most 500,000 Da, at most 600,000 Da, at most 700,000 Da, at most 800,000 Da, at most 900,000 Da, or at most 950,000. In still other aspects of this embodiment, a composition comprises uncrosslinked hyaluronan polymers having a mean molecular weight of, e.g., about 100,000 Da to about 500,000 Da, about 200,000 Da to about 500,000 Da, about 300,000 Da to about 500,000 Da, about 400,000 Da to about 500,000 Da, about 500,000 Da to about 950,000 Da, about 600,000 Da to about 950,000 Da, about 700,000 Da to about 950,000 Da, about 800,000 Da to about 950,000 Da, about 300,000 Da to about 600,000 Da, about 300,000 Da to about 700,000 Da, about 300,000 Da to about 800,000 Da, or about 400,000 Da to about 700,000 Da.

In another embodiment, a composition comprises uncrosslinked hyaluronan polymers of high molecular weight. In aspects of this embodiment, a composition comprises an uncrosslinked hyaluronan having a mean molecular weight of, e.g., about 1,000,000 Da, about 1,500,000 Da, about 2,000,000 Da, about 2,500,000 Da, about 3,000,000 Da, about 3,500,000 Da, about 4,000,000 Da, about 4,500,000 Da, or about 5,000,000 Da. In other aspects of this embodiment, a composition comprises an uncrosslinked hyaluronan polymers having a mean molecular weight of, e.g., at least 1,000,000 Da, at least 1,500,000 Da, at least 2,000,000 Da, at least 2,500,000 Da, at least 3,000,000 Da, at least 3,500,000 Da, at least 4,000,000 Da, at least 4,500,000 Da, or at least 5,000,000 Da. In yet other aspects of this embodiment, a composition comprises an uncrosslinked hyaluronan polymers having a mean molecular weight of, e.g., about 1,000,000 Da to about 5,000,000 Da, about 1,500,000 Da to about 5,000,000 Da, about 2,000.000 Da to about 5,000,000 Da, about 2,500,000 Da to about 5,000,000 Da, about 2,000,000 Da to about 3,000,000 Da, about 2,500,000 Da to about 3,500,000 Da, or about 2,000,000 Da to about 4,000,000 Da. In still other aspects, a composition comprises an uncrosslinked hyaluronan polymers having a mean molecular weight of, e.g., greater than 2,000,000 Da and less than about 3,000,000 Da, greater than 2,000,000 Da and less than about 3,500,000 Da, greater than 2,000,000 Da and less than about 4,000,000 Da, greater than 2,000,000 Da and less than about 4,500,000 Da, greater than 2,000,000 Da and less than about 5,000,000 Da.

In another embodiment, a composition comprises uncrosslinked hyaluronan polymers where the uncrosslinked hyaluronan comprises a combination of both high molecular weight hyaluronan polymers and low molecular weight hyaluronan polymers, in various ratios. In aspects of this embodiment, a composition comprises an uncrosslinked hyaluronan polymers where the uncrosslinked hyaluronan polymers comprises a combination of both high molecular weight hyaluronan polymers and low molecular weight hyaluronan polymers in a ratio of about 20:1, about 15:1, about 10:1, about 5:1, about 1:1, about 1:5 about 1:10, about 1:15, or about 1:20.

Aspects of the present specification provide, in part, a hydrogel composition comprising a substantially uncrosslinked glycosaminoglycan polymer. As sued herein, the term "substantially uncrosslinked" refers to the presence of uncrosslinked glycosaminoglycan polymers in a composition disclosed herein at a level of at least 90% by weight of the composition, with the remaining at most 10% by weight of the composition being comprised of other components including crosslinked glycosaminoglycan polymers. In aspects of this embodiment, a composition comprises a substantially uncrosslinked chondroitin sulfate polymer, a substantially uncrosslinked dermatan sulfate polymer, a substantially uncrosslinked keratan sulfate polymer, a substantially uncrosslinked heparan polymer, a substantially uncrosslinked heparan sulfate polymer, or a substantially uncrosslinked hyaluronan polymer. In other aspects of this embodiment, a composition comprises an uncrosslinked glycosaminoglycan where the uncrosslinked glycosaminoglycan represents, e.g., about 90% or more by weight, about 91% or more by weight, about 92% or more by weight, about 93% or more by weight, about 94% or more by weight, about 95% or more by weight, about 96% or more by weight, about 97% or more by weight, about 98% or more by weight, or about 99% or more, or about 100% by weight, of the total glycosaminoglycan present in the composition. In yet other aspects of this embodiment, a composition comprises an uncrosslinked glycosaminoglycan where the uncrosslinked glycosaminoglycan represents, e.g., about 90% to about 100% by weight, about 93% to about 100% by weight, about 95% to about 100% by weight, or about 97% to about 100% by weight, of the total glycosaminoglycan present in the composition.

Aspects of the present specification provide, in part, a hydrogel composition comprising a ratio of crosslinked glycosaminoglycan polymer and uncrosslinked glycosaminoglycan polymer. This ratio of crosslinked and uncrosslinked glycosaminoglycan polymer is also known as the gel:fluid ratio. Any gel:fluid ratio is useful in making the compositions disclosed herein with the proviso that such ratio produces a composition disclosed herein that improves a skin condition as disclosed herein. Non-limiting examples of gel:fluid ratios include 100:0, 98:2, 90:10, 75:25, 70:30, 60:40, 50:50, 40:60, 30:70, 25:75, 10:90; 2:98, and 0:100.

In aspects of this embodiment, a composition comprises a crosslinked glycosaminoglycan polymer and an uncrosslinked glycosaminoglycan polymer where the gel:fluid ratio is, e.g., about 0:100, about 1:99, about 2:98, about 3:97, about 4:96, about 5:95, about 6:94, about 7:93, about 8:92, about 9:91, or about 10:90. In other aspects of this embodiment, a composition comprises a crosslinked glycosaminoglycan polymer and an uncrosslinked glycosaminoglycan polymer where the gel:fluid ratio is, e.g., at most 1:99, at most 2:98, at most 3:97, at most 4:96, at most 5:95, at most 6:94, at most 7:93, at most 8:92, at most 9:91, or at most 10:90. In yet other aspects of this embodiment, a composition comprises a crosslinked glycosaminoglycan polymer and an uncrosslinked glycosaminoglycan polymer where the gel:fluid ratio is, e.g., about 0:100 to about 3:97, about 0:100 to about 5:95, or about 0:100 to about 10:90.

In other aspects of this embodiment, a composition comprises a crosslinked glycosaminoglycan polymer and an uncrosslinked glycosaminoglycan polymer where the gel:fluid ratio is, e.g., about 15:85, about 20:80, about 25:75, about 30:70, about 35:65, about 40:60, about 45:55, about 50:50, about 55:45, about 60:40, about 65:35, about 70:30, about 75:25, about 80:20, about 85:15, about 90:10, about 95:5, about 98:2, or about 100:0. In yet other aspects of this embodiment, a composition comprises a crosslinked glycosaminoglycan polymer and an uncrosslinked glycosaminoglycan polymer where the gel:fluid ratio is, e.g., at most 15:85, at most 20:80, at most 25:75, at most 30:70, at most 35:65, at most 40:60, at most 45:55, at most 50:50, at most 55:45, at most 60:40, at most 65:35, at most 70:30, at most 75:25, at most 80:20, at most 85:15, at most 90:10, at most 95:5, at most 98:2, or at most 100:0. In still other aspects of this embodiment, a composition comprises a crosslinked glycosaminoglycan polymer and an uncrosslinked glycosaminoglycan polymer where the gel:fluid ratio is, e.g., about 10:90 to about 70:30, about 15:85 to about 70:30, about 10:90 to about 55:45, about 80:20 to about 95:5, about 90:10 to about 100:0, about 75:25 to about 100:0, or about 60:40 to about 100:0.

Aspects of the present specification provide, in part, a hydrogel composition disclosed herein that may optionally comprise an anesthetic agent. An anesthetic agent is preferably a local anesthetic agent, i.e., an anesthetic agent that causes a reversible local anesthesia and a loss of nociception, such as, e.g., aminoamide local anesthetics and aminoester local anesthetics. The amount of an anesthetic agent included in a composition disclosed herein is an amount effective to mitigate pain experienced by an individual upon administration of the composition. As such, the amount of an anesthetic agent included in a composition disclosed in the present specification is between about 0.1% to about 5% by weight of the total composition The anesthetic agent may be any suitable anesthetic agent, for example, but not limited to lidocaine. A composition disclosed herein may comprise a single anesthetic agent or a plurality of anesthetic agents. A non-limiting example of a combination local anesthetic is lidocaine/prilocaine (EMLA).

The anesthetic agent may be present in the composition in an amount of, e.g., about 0.1%, about 0.2%, about 0.3%, about 0.4%, about 0.5%, about 0.6%, about 0.7%, about 0.8%, about 0.9%, about 1.0%, about 2.0%, about 3.0%, about 4.0%, about 5.0%., or more, by weight of the total composition. In further aspects, a composition disclosed herein comprises an anesthetic agent in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.2% to about 0.9%, about 0.2% to about 1.0%, about 0.2% to about 2.0%, about 0.5% to about 1.0%, or about 0.5% to about 2.0% by weight of the total composition.

The amount of an anti-oxidant agent included in a composition disclosed herein is an amount effective to reduce or prevent degradation of the composition, such as, e.g., oxidative stresses, enzymatic degradation and/or chemical degradation of the composition. The amount of an anti-oxidant agent included in a composition disclosed herein may be between about 0.1% to about 10% by weight of the total composition.

Aspects of the present specification provide, in part, a hydrogel composition disclosed herein that may comprise a flavonoid (Table 2). A flavonoid (or bioflavonoid) refers to the class of polyphenolic ketone-containing and non-ketone-containing secondary metabolites found in plants that are well known to have diverse beneficial biochemical and antioxidant effects. Non-limiting examples of flavonoids include C-methylated flavonoids, O-methylated flavonoids, isoflavonoids, neoflavonoids, flavonolignans, furanoflavonoids, pyranoflavonoids, methylenedioxyflavonoids, prenylated flavonoids, aurones, flavones, flavonols, flavanones, flavanonols, flavan-3-ols, flavan-4-ols, leucoanthocyanidin (flavan-3,4-diols), anthocyanidins, and tannins.

In some preferred embodiments, the antioxidant agent is a water soluble flavonoid, for example, a glucosylated flavonoid, for example, Epigallocatechin Gallatyl Glucoside (e.g. Inoveol® EGCG).

Aurones are flavonoid compounds derived from 2-benzylidene-1-benzofuran-3-one. Non-limiting examples of aurones include 4,5,6-trihydroxy-aurone, aureusidin, hispidol, leptosidin, maritimetin, and sulfuretin.

Three major classes of ketone-containing flavonoids are flavones, compounds derived from 2-phenylchromen-4-one (2-phenyl-1,4-benzopyrone); isoflavones, compounds derived from 3-phenylchromen-4-one (3-phenyl-1,4-benzopyrone); and neoflavones, compounds derived from 4-phenylcoumarine (4-phenyl-1,2-benzopyrone) (Table 2). Flavones are themselves divided into four groups based on the presence or absence of 3-hydroxyl 2,3-dihydro functional groups: flavones, compounds derived from 2-phenylchromen-4-one lack both functional groups; flavonols (3-hydroxyflavone), compounds derived from 3-hydroxy-2-phenylchromen-4-one have the 3-hydroxyl group, but lack the 2,3-dihydro group; flavanones, compounds derived from 2,3-dihydro-2-phenylchromen-4-one have the 2,3-dihydro group, but lack the 3-hydroxyl group; and flavanonols (3-hydroxyflavanone or 2,3-dihydroflavonol), compounds derived from 3-hydroxy-2,3-dihydro-2-phenylchromen-4-one have both functional groups.

Non-limiting examples of flavones include acacetin, apiin, apigenin, apigetrin, artoindonesianin P, baicalein, baicalin, chrysin, cynaroside, diosmetin, diosmin, eupatilin, flavoxate, 6-hydroxyflavone, genkwanin, hidrosmin, luteolin, nepetin, nepitrin (nepetin 7-glucoside), nobiletin, orientin (isoorientin), oroxindin, oroxylin A, rhoifolin, scutellarein, scutellarin, tangeritin, techtochrysin, tetuin, tricin, veronicastroside, vitexin (isovitexin), and wogonin. Non-limiting examples of flavonols include 3-hydroxyflavone, azaleatin, fisetin, galangin, gossypetin, kaempferide, kaempferol, isorhamnetin, morin, myricetin, natsudaidain, pachypodol, quercetin, rhamnazin, rhamnetin, and sophorin. Non-limiting examples of flavanones include butin, eriodictyol, hesperetin, hesperidin, homoeriodictyol, isosakuranetin, naringenin, naringin, pinocembrin, poncirin, sakuranetin, sakuranin, and sterubin. Non-limiting examples of flavanonols include taxifolin (dihydroquercetin), and aromadedrin (dihydrokaempferol).

Isoflavonoids include isoflavones and isoflavanes (Table 2). Non-limiting examples of isoflavonoids include alpinumisoflavone, anagyroidisoflavone A and B, calycosin, daidzein, daidzin, derrubone, di-O-methylalpinumisoflavone, formononetin, genistein, genistin, glycitein, ipriflavone, irigenin, iridin, irilone, 4'-methyl-alpinumisoflavone, 5-O-methylgenistein, luteone, ononin, orobol, pratensein, prunetin, pseudobaptigenin, psi-tectorigenin, puerarin, retusin, tectoridin, tectorigenin, and wighteone.

Neoflavonoids include 4-arylcoumarins (neoflavones), 4-arylchromanes, dalbergiones and dalbergiquinols (Table 2). Neoflavones are compounds derived from 4-phenylcoumarin (or 4-Aryl-coumarin); neoflavenes compounds derived from 4-phenylchromen. Non-limiting examples of neoflavonoids include calophyllolide, coutareagenin, dalbergichromene, dalbergin, and nivetin.

Non-ketone-containing flavonoids include flavan-3-ols and catechins. Flavan-3-ols (flavanols) are a class of flavonoids derived from 2-phenyl-3,4-dihydro-2H-chromen-3-ol skeleton. Catechin possesses two benzene rings (called the A- and B-rings) and a dihydropyran heterocycle (the C-ring) with an hydroxyl group on carbon 3. The A ring is similar to a resorcinol moiety while the B ring is similar to a catechol moiety. There are two chiral centers on the molecule on carbons 2 and 3. It has therefore four diastereoisomers. Two of the isomers are in trans configuration and are called catechin and the other two are in cis configuration and are called epicatechin. Non-limiting examples of non-ketone-containing flavonoids include afzelechin, arthromerin A, arthromerin B, catechin, epicatechin, epigallocatechin, epicatechin gallate, epigallocatechin gallate, epigallocatechin gallate, epiafzelechin, fisetinidol, gallocatechin, gallocatechin gallate, guibourtinidol, meciadanol (3-O-methylcatechin), mesquitol, propyl gallate, robinetinidol, and thearubigin.

Flavan-4-ols (3-deoxyflavonoids) are flavone-derived alcohols derived from 2-phenylchroman-4-ol. Non-limiting examples of flavan-4-ols include apiforol and luteoforol.

Leucoanthocyanidin (flavan-3,4-diols) are compounds derived from 2-phenyl-3,4-dihydro-2H-chromene-3,4-diol. Non-limiting examples of flavan-3,4-diols include leucocyanidin, leucodelphinidin, leucomalvidin, leucopelargonidin, leucopeonidin, leucorobinetinidin, and melacacidin.

Anthocyanidins are compounds derived from 2-phenylchromenylium. Non-limiting examples of anthocyanidins include antirrhinin, apigeninidin, aurantinidin, capensinidin, chrysanthenin, columnidin, commelinin, cyanidin, 6-hydroxycyanidin, cyanidin-3-(di-p-coumarylglucoside)-5-glucoside, cyanosalvianin, delphinidin, diosmetinidin, europinidin, fisetinidin, gesneridin, guibourtinidin, hirsutidin, luteolinidin, malvidin, 5-desoxy-malvidin, malvin, myrtillin, oenin, peonidin, 5-desoxy-peonidin, pelargonidin, petunidin, primulin, protocyanin, protodelphin, pulchellidin, pulchellidin 3-glucoside, pulchellidin 3-rhamnoside, robinetinidin, rosinidin, tricetinidin, tulipanin, and violdelphin.

Tannins are compounds derived from 2-phenylchromenylium. There are three major classes of tannins: hydrolyzable tannins; non-hydrolyzable tannins (condensed tannins; proanthocyanidins); and pseudotannins.

Hydrolyzable tannins are themselves divided into four groups: oligomer tannins including aglycone tannins and glycoside tannins; ellagitannins; gallotannins, and unclassified tannins. Non-limiting examples of aglycone tannins include ellagic acid, gallagic acid, and gallic acid. Non-limiting examples of glycoside tannins include glucose, quinic acid, and shikimic acid. Non-limiting examples of ellagitannins include castalagin (vescalagin), castalin, casuarictin, casuariin, casuarinin, cornusiin E, grandinin, pedunculagin, punicacortein C, punigluconin, punicalagin, punicalagin alpha, punicalin, 2-O-galloyl-punicalin, stachyurin, strictinin, and tellimagrandin II. Non-limiting examples of gallotannins include corilagin, galloyl glucose, digalloyl glucose, trigalloyl glucose, tetragalloyl glucose, pentagalloyl glucose, hexagalloyl glucose, heptagalloyl glucose, octagalloyl glucose, and tannic acid. Non-limiting examples of unclassified tannins include acutissimin A, acutissimin B, chebulagic acid, chebulinic acid, cinnamtannin B1, combreglutinin, geraniin, granatin B, roburin A, roburin B, roburin C, roburin D, roburin E, stachyurin, tercatin, terflavins A, terflavins B, tergallagin, vescalin, 1,3,4-tri-O-galloylquinic acid, 3,5-di-O-galloyl-shikimic acid, and 3,4,5-tri-O-galloylshikimic acid.

Condensed tannins (proanthocyanidins) are essentially polymer chains of flavonoids such as catechins. Non-limiting examples of condensed tannins include proanthocyanidin, prodelphinidin, profisetinidin, proguibourtinidin, and prorobinetidin.

TABLE 2

Flavonoids

| Flavonoids | Base compound | Examples |
|---|---|---|
| Aurones | 2-benzylidene-1-benzofuran-3-one | 4,5,6-trihydroxy-aurone, aureusidin, hispidol, leptosidin, maritimetin, and sulfuretin |
| Flavones | 2-phenylchromen-4-one | acacetin, apiin, apigenin, apigetrin, artoindonesianin P, baicalein, baicalin, chrysin, cynaroside, diosmetin, diosmin, eupatilin, flavoxate, 6-hydroxyflavone, genkwanin, hidrosmin, luteolin, nepetin, nepitrin, nobiletin, orientin, oroxindin, oroxylin A, rhoifolin, scutellarein, scutellarin, tangeritin, techtochrysin, tetuin, tricin, veronicastroside, vitexin, wogonin |
| Flavonols | 3-hydroxy-2-phenyl-chromen-4-one | 3-hydroxyflavone, azaleatin, fisetin, galangin, gossypetin, kaempferide, kaempferol, isorhamnetin, morin, myricetin, natsudaidain, pachypodol, quercetin, rhamnazin, rhamnetin, sophorin |
| Flavanones | 2,3-dihydro-2-phenyl-chromen-4-one | butin, eriodictyol, hesperetin, hesperidin, homoeriodictyol, isosakuranetin, naringenin, naringin, pinocembrin, poncirin, sakuranetin, sakuranin, sterubin |
| Flavanonols | 3-hydroxy-2,3-dihydro-2-phenylchromen-4-one | aromadedrin, taxifolin |
| Isoflavones | 3-phenylchromen-4-one | alpinumisoflavone, anagyroidisoflavone A and B, calycosin, daidzein, daidzin, derrubone, di-O-methylalpinumisoflavone, formononetin, genistein, genistin, glycitein, ipriflavone, irigenin, iridin, irilone, 4'-methyl-alpinumisoflavone, 5-O-methylgenistein, luteone, ononin, orobol, pratensein, prunetin, pseudobaptigenin, psi-tectorigenin, puerarin, retusin, tectoridin, tectorigenin, wighteone |
| Isoflavenes | 3-phenylchroman | lonchocarpane, laxiflorane |
| Neoflavones | 4-phenylcoumarine | calophyllolide |
| Neoflavenes | 4-phenylchromen | dalbergichromene |
| Flavan-3-ols | 2-phenyl-3,4-dihydro-2H-chromen-3-ol | arthromerin A, arthromerin B, fisetinidol, guibourtinidol, meciadanol (3-O-methylcatechin), mesquitol, robinetinidol, thearubigin. |
| Catechins | (2R,3S)-2-(3,4-dihydroxyphenyl)-3,4-dihydro-2H-chromene-3,5,7-triol | (+)-catechin (2R-3S), (−)-catechin (2S-3R), (−)-Epicatechin (2R-3R), (+)-epicatechin (2S-3S) |
| Flavan-4-ols | 2-phenylchroman-4-ol | apiforol, luteoforol |
| Flavan-3,4-diols | 2-phenyl-3,4-dihydro-2H-chromene-3,4-diol | leucocyanidin, leucodelphinidin, leucomalvidin, leucopelargonidin, leucopeonidin, leucorobinetinidin, melacacidin |
| Anthocyanidins | 2-phenylchromenylium | antirrhinin, apigeninidin, aurantinidin, capensinidin, chrysanthenin, columnidin, commelinin, cyanidin, 6-hydroxycyanidin, cyanidin-3-(di-p- |

TABLE 2-continued

| Flavonoids | | |
|---|---|---|
| Flavonoids | Base compound | Examples |
| | | coumarylglucoside)-5-glucoside, cyanosalvianin, delphinidin, diosmetinidin, europinidin, fisetinidin, gesneridin, guibourtinidin, hirsutidin, luteolinidin, malvidin, 5-desoxy-malvidin, malvin, myrtillin, oenin, peonidin, 5-desoxy-peonidin, pelargonidin, petunidin, primulin, protocyanin, protodelphin, pulchellidin, pulchellidin 3-glucoside, pulchellidin 3-rhamnoside, robinetinidin, rosinidin, tricetinidin, tulipanin, violdelphin |
| Hydrolyzable tannins | gallic acid or ellagic acid | castalagin, castalin, casuarictin, casuariin, casuarinin, corilagin, cornusiin E, grandinin, galloyl glucose, digalloyl glucose, trigalloyl glucose, tetragalloyl glucose, pentagalloyl glucose, hexagalloyl glucose, heptagalloyl glucose, octagalloyl glucose, pedunculagin, punicacortein C, punigluconin, punicalagin, punicalagin alpha, punicalin, 2-O-galloyl-punicalin, stachyurin, strictinin, tannic acid, tellimagrandin II |
| Condensed tannins | polymer chains of flavonoid units | proanthocyanidin, prodelphinidin, profisetinidin, proguibourtinidin, prorobinetidin |

Aspects of the present specification provide, in part, a hydrogel composition disclosed herein that may optionally comprise a flavonoid-type phytoalexin. A phytoalexin refers to the class of antimicrobial molecules with antioxidant effects synthesized de novo by plants in response to an incompatible pathogen infection. Non-limiting examples of phytoalexins include resveratrol (3,5,4'-trihydroxy-trans-stilbene), allixin (3-hydroxy-5-methoxy-6-methyl-2-pentyl-4H-pyran-4-one), glyceollin, phaseolin, and medicarpin.

In an embodiment, a composition disclosed herein comprises at least one antioxidant agent in an amount sufficient to reduce or prevent degradation of a glycosaminoglycan polymer.

In other aspects of this embodiment, a composition disclosed herein comprises an antioxidant agent in an amount of, e.g., about 0.01%, about 0.1%, about 0.2%, about 0.3%, about 0.4%, about 0.5%, about 0.6%, about 0.7%, about 0.8% about 0.9%, about 1.0%, about 2.0%, about 3.0%, about 4.0%, about 5.0%, about 6.0%, about 7.0%, about 8.0%, about 9.0%, or about 10% by weight of the total composition. In yet other aspects, a composition disclosed herein comprises an antioxidant agent in an amount of, e.g., at least 0.1%, at least 0.2%, at least 0.3%, at least 0.4%, at least 0.5%, at least 0.6%, at least 0.7%, at least 0.8% at least 0.9%, at least 1.0%, at least 2.0%, at least 3.0%, at least 4.0%, at least 5.0%, at least 6.0%, at least 7.0%, at least 8.0%, at least 9.0%, or at least 10% by weight of the total composition. In still other aspects, a composition disclosed herein comprises an antioxidant agent in an amount of, e.g., at most 0.1%, at most 0.2%, at most 0.3%, at most 0.4%, at most 0.5%, at most 0.6%, at most 0.7%, at most 0.8% at most 0.9%, at most 1.0%, at most 2.0%, at most 3.0%, at most 4.0%, at most 5.0%, at most 6.0%, at most 7.0%, at most 8.0%, at most 9.0%, or at most 10% by weight of the total composition. In further aspects, a composition disclosed herein comprises an antioxidant agent in an amount of, e.g., about 0.1% to about 0.5%, about 0.1% to about 1.0%, about 0.1% to about 2.0%, about 0.1% to about 3.0%, about 0.1% to about 4.0%, about 0.1% to about 5.0%, about 0.2% to about 0.9%, about 0.2% to about 1.0%, about 0.2% to about 2.0%, about 0.5% to about 1.0%, or about 0.5% to about 2.0% by weight of the total composition.

Aspects of the present specification provide, in part, a hydrogel composition disclosed herein that exhibits a complex modulus, an elastic modulus, a viscous modulus and/or a tan δ. The compositions as disclosed herein are viscoelastic in that the composition has an elastic component (solid-like such as, e.g., crosslinked glycosaminoglycan polymers) and a viscous component (liquid-like such as, e.g., uncross-linked glycosaminoglycan polymers or a carrier phase) when a force is applied (stress, deformation). The rheological attribute that described this property is the complex modulus (G*), which defines a composition's total resistance to deformation. The complex modulus is a complex number with a real and imaginary part: $G^* = G' + iG''$. The absolute value of G* is $Abs(G^*) = Sqrt(G'^2 + G''^2)$. The complex modulus can be defined as the sum of the elastic modulus (G') and the viscous modulus (G'').

The complex modulus describes the interaction between elasticity and strength (G*=stress/strain) and, as such, provides a quantitative measurement of a composition's hardness or softness; stress is the force causing the deformation divided by the area to which the force is applied; and strain is the ratio of the change caused by the stress to the original state of the object. Although depending on the speed at which the force is applied, a stiffer composition will have a higher complex modulus (and usually a higher elastic modulus in the case of crosslinked fillers) and it will take a greater force to deform the material a given distance, such as, e.g., an injection. Complex modulus can be decomposed into an elastic modulus and a viscous modulus, reflecting the fact that the compositions of the invention have viscoelasric properties. Elastic modulus, or modulus of elasticity, refers to the ability of a hydrogel material to recover from shear deformation, or, conversely, an object's tendency to be non-permanently deformed when a force is applied to it. Elastic modulus characterizes the elastic recovery of a composition and is also known as the storage modulus because it describes how much energy is stored upon shear deformation of the composition.

Viscous modulus is also known as the loss modulus because it describes the energy that is lost as heat dissipation during shear deformation. Tan δ is the ratio of the viscous modulus and the elastic modulus, tan δ=G''/G'. For tan δ values disclosed in the present specification, a tan δ is obtained from the elastic/viscous modulus at a frequency of 1 Hz. A lower tan δ corresponds to a more elastic composition. For fillers described in this invention, complex, elastic and viscous modulus are usually measured through shear deformation in oscillation mode (with a sinusoidal input and response).

In another embodiment, a hydrogel composition disclosed herein exhibits an elastic modulus. In aspects of this embodiment, a hydrogel composition exhibits an elastic modulus of, e.g., about 25 Pa, about 50 Pa, about 75 Pa, about 100 Pa, about 125 Pa, about 150 Pa, about 175 Pa, about 200 Pa, about 250 Pa, about 300 Pa, about 350 Pa, about 400 Pa, about 450 Pa, about 500 Pa, about 550 Pa, about 600 Pa, about 650 Pa, about 700 Pa, about 750 Pa, about 800 Pa, about 850 Pa, about 900 Pa, about 950 Pa, about 1,000 Pa, about 1,200 Pa, about 1,300 Pa, about 1,400 Pa, about 1,500

Pa, about 1,600 Pa, about 1700 Pa, about 1800 Pa, about 1900 Pa, about 2,000 Pa, about 2,100 Pa, about 2,200 Pa, about 2,300 Pa, about 2,400 Pa, or about 2,500 Pa. In other aspects of this embodiment, a hydrogel composition exhibits an elastic modulus of, e.g., at least 25 Pa, at least 50 Pa, at least 75 Pa, at least 100 Pa, at least 125 Pa, at least 150 Pa, at least 175 Pa, at least 200 Pa, at least 250 Pa, at least 300 Pa, at least 350 Pa, at least 400 Pa, at least 450 Pa, at least 500 Pa, at least 550 Pa, at least 600 Pa, at least 650 Pa, at least 700 Pa, at least 750 Pa, at least 800 Pa, at least 850 Pa, at least 900 Pa, at least 950 Pa, at least 1,000 Pa, at least 1,200 Pa, at least 1,300 Pa, at least 1,400 Pa, at least 1,500 Pa, at least 1,600 Pa, at least 1700 Pa, at least 1800 Pa, at least 1900 Pa, at least 2,000 Pa, at least 2,100 Pa, at least 2,200 Pa, at least 2,300 Pa, at least 2,400 Pa, or at least 2500 Pa. In yet other aspects of this embodiment, a hydrogel composition exhibits an elastic modulus of, e.g., at most 25 Pa, at most 50 Pa, at most 75 Pa, at most 100 Pa, at most 125 Pa, at most 150 Pa, at most 175 Pa, at most 200 Pa, at most 250 Pa, at most 300 Pa, at most 350 Pa, at most 400 Pa, at most 450 Pa, at most 500 Pa, at most 550 Pa, at most 600 Pa, at most 650 Pa, at most 700 Pa, at most 750 Pa, at most 800 Pa, at most 850 Pa, at most 900 Pa, at most 950 Pa, at most 1,000 Pa, at most 1,200 Pa, at most 1,300 Pa, at most 1,400 Pa, at most 1,500 Pa, or at most 1,600 Pa. In still other aspects of this embodiment, a hydrogel composition exhibits an elastic modulus of, e.g., about 25 Pa to about 150 Pa, about 25 Pa to about 300 Pa, about 25 Pa to about 500 Pa, about 25 Pa to about 800 Pa, about 125 Pa to about 300 Pa, about 125 Pa to about 500 Pa, about 125 Pa to about 800 Pa, about 500 Pa to about 1,600 Pa, about 600 Pa to about 1,600 Pa, about 700 Pa to about 1,600 Pa, about 800 Pa to about 1,600 Pa, about 900 Pa to about 1,600 Pa, about 1,000 Pa to about 1,600 Pa, about 1,100 Pa to about 1,600 Pa, about 1,200 Pa to about 1,600 Pa, about 500 Pa to about 2,500 Pa, about 1,000 Pa to about 2,500 Pa, about 1,500 Pa to about 2,500 Pa, about 2,000 Pa to about 2,500 Pa, about 1,300 Pa to about 1,600 Pa, about 1,400 Pa to about 1,700 Pa, about 1,500 Pa to about 1,800 Pa, about 1,600 Pa to about 1,900 Pa, about 1,700 Pa to about 2,000 Pa, about 1,800 Pa to about 2,100 Pa, about 1,900 Pa to about 2,200 Pa, about 2,000 Pa to about 2,300 Pa, about 2,100 Pa to about 2,400 Pa, or about 2,200 Pa to about 2,500 Pa.

In another embodiment, a hydrogel composition disclosed herein exhibits a viscous modulus. In aspects of this embodiment, a hydrogel composition exhibits a viscous modulus of, e.g., about 10 Pa, about 20 Pa, about 30 Pa, about 40 Pa, about 50 Pa, about 60 Pa, about 70 Pa, about 80 Pa, about 90 Pa, about 100 Pa, about 150 Pa, about 200 Pa, about 250 Pa, about 300 Pa, about 350 Pa, about 400 Pa, about 450 Pa, about 500 Pa, about 550 Pa, about 600 Pa, about 650 Pa, or about 700 Pa. In other aspects of this embodiment, a hydrogel composition exhibits a viscous modulus of, e.g., at most 10 Pa, at most 20 Pa, at most 30 Pa, at most 40 Pa, at most 50 Pa, at most 60 Pa, at most 70 Pa, at most 80 Pa, at most 90 Pa, at most 100 Pa, at most 150 Pa, at most 200 Pa, at most 250 Pa, at most 300 Pa, at most 350 Pa, at most 400 Pa, at most 450 Pa, at most 500 Pa, at most 550 Pa, at most 600 Pa, at most 650 Pa, or at most 700 Pa. In yet other aspects of this embodiment, a hydrogel composition exhibits a viscous modulus of, e.g., about 10 Pa to about 30 Pa, about 10 Pa to about 50 Pa, about 10 Pa to about 100 Pa, about 10 Pa to about 150 Pa, about 70 Pa to about 100 Pa, about 50 Pa to about 350 Pa, about 150 Pa to about 450 Pa, about 250 Pa to about 550 Pa, about 350 Pa to about 700 Pa, about 50 Pa to about 150 Pa, about 100 Pa to about 200 Pa, about 150 Pa to about 250 Pa, about 200 Pa to about 300 Pa, about 250 Pa to about 350 Pa, about 300 Pa to about 400 Pa, about 350 Pa to about 450 Pa, about 400 Pa to about 500 Pa, about 450 Pa to about 550 Pa, about 500 Pa to about 600 Pa, about 550 Pa to about 650 Pa, or about 600 Pa to about 700 Pa.

In another embodiment, a hydrogel composition disclosed herein exhibits a tan δ. In aspects of this embodiment, a hydrogel composition exhibits a tan δ of, e.g., about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, or about 2.5. In other aspects of this embodiment, a hydrogel composition exhibits a tan δ of, e.g., at most 0.1, at most 0.2, at most 0.3, at most 0.4, at most 0.5, at most 0.6, at most 0.7, at most 0.8, at most 0.9, at most 1.0, at most 1.1, at most 1.2, at most 1.3, at most 1.4, at most 1.5, at most 1.6, at most 1.7, at most 1.8, at most 1.9, at most 2.0, at most 2.1, at most 2.2, at most 2.3, at most 2.4, or at most 2.5. In yet other aspects of this embodiment, a hydrogel composition exhibits a tan δ of, e.g., about 0.1 to about 0.3, about 0.3 to about 0.5, about 0.5 to about 0.8, about 1.1 to about 1.4, about 1.4 to about 1.7, about 0.3 to about 0.6, about 0.1 to about 0.5, about 0.5 to about 0.9, about 0.1 to about 0.6, about 0.1 to about 1.0, about 0.5 to about 1.5, about 1.0 to about 2.0, or about 1.5 to about 2.5. In some embodiments the tan δ is less than about 0.1, for example, is about 0.02 to about 0.1, for example, about 0.05.

Aspects of the present specification provide, in part, a hydrogel composition disclosed herein having a transparency and/or translucency. Transparency (also called pellucidity or diaphaneity) is the physical property of allowing light to pass through a material, whereas translucency (also called translucence or translucidity) only allows light to pass through diffusely. The opposite property is opacity. Transparent materials are clear, while translucent ones cannot be seen through clearly. The silk fibroin hydrogels disclosed herein may, or may not, exhibit optical properties such as transparency and translucency. In certain cases, e.g., superficial line filling, it would be an advantage to have an opaque hydrogel. In other cases such as development of a lens or a "humor" for filling the eye, it would be an advantage to have a translucent hydrogel. These properties could be modified by affecting the structural distribution of the hydrogel material. Factors used to control a hydrogel's optical properties include, without limitation, polymer concentration, gel crystallinity, and hydrogel homogeneity.

When light encounters a material, it can interact with it in several different ways. These interactions depend on the nature of the light (its wavelength, frequency, energy, etc.) and the nature of the material. Light waves interact with an object by some combination of reflection, and transmittance with refraction. As such, an optically transparent material allows much of the light that falls on it to be transmitted, with little light being reflected. Materials which do not allow the transmission of light are called optically opaque or simply opaque.

In an embodiment, a hydrogel composition disclosed herein is optically transparent. In aspects of this embodiment, a hydrogel composition transmits, e.g., about 75% of the light, about 80% of the light, about 85% of the light, about 90% of the light, about 95% of the light, or about 100% of the light. In other aspects of this embodiment, a hydrogel composition transmits, e.g., at least 75% of the light, at least 80% of the light, at least 85% of the light, at least 90% of the light, or at least 95% of the light. In yet other aspects of this embodiment, a hydrogel composition transmits, e.g., about 75% to about 100% of the light, about 80% to about 100% of the light, about 85% to about 100% of the light, about 90% to about 100% of the light, or about 95% to about 100% of the light.

In another embodiment, a hydrogel composition disclosed herein is optically opaque. In aspects of this embodiment, a hydrogel composition transmits, e.g., about 5% of the light, about 10% of the light, about 15% of the light, about 20% of the light, about 25% of the light, about 30% of the light, about 35% of the light, about 40% of the light, about 45% of the light, about 50% of the light, about 55% of the light, about 60% of the light, about 65% of the light, or about 70% of the light. In other aspects of this embodiment, a hydrogel composition transmits, e.g., at most 5% of the light, at most 10% of the light, at most 15% of the light, at most 20% of the light, at most 25% of the light, at most 30% of the light, at most 35% of the light, at most 40% of the light, at most 45% of the light, at most 50% of the light, at most 55% of the light, at most 60% of the light, at most 65% of the light, at most 70% of the light, or at most 75% of the light. In other aspects of this embodiment, a hydrogel composition transmits, e.g., about 5% to about 15%, about 5% to about 20%, about 5% to about 25%, about 5% to about 30%, about 5% to about 35%, about 5% to about 40%, about 5% to about 45%, about 5% to about 50%, about 5% to about 55%, about 5% to about 60%, about 5% to about 65%, about 5% to about 70%, about 5% to about 75%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 15% to about 65%, about 15% to about 70%, about 15% to about 75%, about 25% to about 35%, about 25% to about 40%, about 25% to about 45%, about 25% to about 50%, about 25% to about 55%, about 25% to about 60%, about 25% to about 65%, about 25% to about 70%, or about 25% to about 75%, of the light.

In an embodiment, a hydrogel composition disclosed herein is optically translucent. In aspects of this embodiment, a hydrogel composition diffusely transmits, e.g., about 75% of the light, about 80% of the light, about 85% of the light, about 90% of the light, about 95% of the light, or about 100% of the light. In other aspects of this embodiment, a hydrogel composition diffusely transmits, e.g., at least 75% of the light, at least 80% of the light, at least 85% of the light, at least 90% of the light, or at least 95% of the light. In yet other aspects of this embodiment, a hydrogel composition diffusely transmits, e.g., about 75% to about 100% of the light, about 80% to about 100% of the light, about 85% to about 100% of the light, about 90% to about 100% of the light, or about 95% to about 100% of the light.

A hydrogel composition disclosed herein may be further processed by pulverizing the hydrogel into particles and optionally mixed with a carrier phase such as, e.g., water or a saline solution to form an injectable or topical substance like a solution, oil, lotion, gel, ointment, cream, slurry, salve, or paste. As such, the disclosed hydrogel compositions may be monophasic or multiphasic compositions. A hydrogel may be milled to a particle size from about 10 µm to about 1000 µm in diameter, such as about 15 µm to about 30 µm, about 50 µm to about 75 µm, about 100 µm to about 150 µm, about 200 µm to about 300 µm, about 450 µm to about 550 µm, about 600 µm to about 700 µm, about 750 µm to about 850 µm, or about 900 µm to about 1,000 µm.

Aspects of the present specification provide, in part, a composition disclosed herein is injectable. As used herein, the term "injectable" refers to a material having the properties necessary to administer the composition into a skin region of an individual using an injection device with a fine needle. As used herein, the term "thin needle" refers to a needle that is 27 gauge or smaller.

In aspect of this embodiment, a hydrogel composition disclosed herein is injectable through a fine needle. In other aspects of this embodiment, a hydrogel composition disclosed herein is injectable through a needle of, e.g., about 27 gauge, about 30 gauge, or about 32 gauge. In yet other aspects of this embodiment, a hydrogel composition disclosed herein is injectable through a needle of, e.g., 22 gauge or smaller, 27 gauge or smaller, 30 gauge or smaller, or 32 gauge or smaller. In still other aspects of this embodiment, a hydrogel composition disclosed herein is injectable through a needle of, e.g., about 22 gauge to about 35 gauge, 22 gauge to about 34 gauge, 22 gauge to about 33 gauge, 22 gauge to about 32 gauge, about 22 gauge to about 27 gauge, or about 27 gauge to about 32 gauge.

In aspects of this embodiment, a hydrogel composition disclosed herein can be injected with an extrusion force of about 60 N, about 55 N, about 50 N, about 45 N, about 40 N, about 35 N, about 30 N, about 25 N, about 20 N, or about 15 N at speeds of 100 mm/min. In other aspects of this embodiment, a hydrogel composition disclosed herein can be injected through a 27 gauge needle with an extrusion force of about 60 N or less, about 55 N or less, about 50 N or less, about 45 N or less, about 40 N or less, about 35 N or less, about 30 N or less, about 25 N or less, about 20 N or less, about 15 N or less, about 10 N or less, or about 5 N or less. In yet other aspects of this embodiment, a hydrogel composition disclosed herein can hp injected through a 30 gauge needle with an extrusion force of about 60 N or less, about 55 N or less, about 50 N or less, about 45 N or less, about 40 N or less, about 35 N or less, about 30 N or less, about 25 N or less, about 20 N or less, about 15 N or less, about 10 N or less, or about 5 N or less. In still other aspects of this embodiment, a hydrogel composition disclosed herein can be injected through a 32 gauge needle with an extrusion force of about 60 N or less, about 55 N or less, about 50 N or less, about 45 N or less, about 40 N or less, about 35 N or less, about 30 N or less, about 25 N or less, about 20 N or less, about 15 N or less, about 10 N or less, or about 5 N or less.

Aspects of the present specification provide, in part, a hydrogel composition disclosed herein that exhibits cohesivity. Cohesivity, also referred to as internal adhesion, or cohesive force, is a macroscopic property of a material, caused by the intermolecular attraction forces between HA chains within the material that acts to make the HA domains/particles adhere together more or less. Cohesivity is measured through resistance to linear compression and expressed in terms of grams-force (gmf). Cohesivity is affected by, among other factors, the HA concentration, the molecular weight ratio of the initial free glycosaminoglycan polymer, the amount of residual free glycosaminoglycan polymers following crosslinking, and the pH of the hydrogel composition. A composition should be sufficiently cohesive as to remain localized to a site of administration. Additionally, in certain applications, a sufficient cohesivity is important for a composition to retain its shape under linear compression (=flattening), and thus functionality, in the event of mechanical load cycling. As such, in one embodiment, a hydrogel composition disclosed herein exhibits cohesivity, on par with water. In yet another embodiment, a hydrogel composition disclosed herein exhibits sufficient cohesivity to remain localized to a site of administration. In still another embodiment, a hydrogel composition disclosed herein exhibits sufficient cohesivity to retain its shape.

Specifically, a force of 20 gmf (0.1962 N) or more indicates a cohesive material in the sense of the present invention. Gels with lower compression force values are generally not considered cohesive in the context of the present invention. Preferably, the compression force measured as outlined above is at least 25, 30 or 40 gmf. Most preferably, the compression force measured as outlined above is at least 50 or 60 gmf. The precision of this measurement is in the order of ±5 gmf. This is most important for a dermal filler as the cohesivity as defined above will contribute to the lift capacity (clinically called the volumizing/bulking effect) provided by the gel clinically, along with its elastic modulus G'. While cohesive gels can show a good volumizing effect, non-cohesive or weakly cohesive materials with a similar elastic modulus exhibits lower lift capacity due to the non-cohesive gel material spreading more than a more cohesive material when submitted to vertical compression.

Aspects of the present specification provide, in part, a hydrogel composition disclosed herein that exhibits a physiologically-acceptable osmolarity. As used herein, the term "osmolarity" refers to the concentration of osmotically active solutes in solution. As used herein, the term "a physiologically-acceptable osmolarity" refers to an osmolarity in accord with, or characteristic of, the normal functioning of a living organism. As such, administration of a hydrogel composition as disclosed herein exhibits an osmolarity that has substantially no long term or permanent detrimental effect when administered to a mammal. Osmolarity is expressed in terms of osmoles of osmotically active solute per liter of solvent (Osmol/L or Osm/L). Osmolarity is distinct from molarity because it measures moles of osmotically active solute particles rather than moles of solute. The distinction arises because some compounds can dissociate in solution, whereas others cannot. The osmolarity of a solution can be calculated from the following expression: Osmol/L=$\Sigma\ \varphi_i\ \eta_i\ C_i$, where $\varphi$ is the osmotic coefficient, which accounts for the degree of non-ideality of the solution; $\eta$ is the number of particles (e.g. ions) into which a molecule dissociates; and C is the molar concentration of the solute; and i is the index representing the identity of a particular solute. The osmolarity of a hydrogel composition disclosed herein can be measured using a conventional method that measures solutions.

In an embodiment, a hydrogel composition disclosed herein exhibits a physiologically-acceptable osmolarity. In aspects of this embodiment, a hydrogel composition exhibits an osmolarity of, e.g., about 100 mOsm/L, about 150 mOsm/L, about 200 mOsm/L, about 250 mOsm/L, about 300 mOsm/L, about 350 mOsm/L, about 400 mOsm/L, about 450 mOsm/L, or about 500 mOsm/L. In other aspects of this embodiment, a hydrogel composition exhibits an osmolarity of, e.g., at least 100 mOsm/L, at least 150 mOsm/L, at least 200 mOsm/L, at least 250 mOsm/L, at least 300 mOsm/L, at least 350 mOsm/L, at least 400 mOsm/L, at least 450 mOsm/L, or at least 500 mOsm/L. In yet other aspects of this embodiment, a hydrogel composition exhibits an osmolarity of, e.g., at most 100 mOsm/L, at most 150 mOsm/L, at most 200 mOsm/L, at most 250 mOsm/L, at most 300 mOsm/L, at most 350 mOsm/L, at most 400 mOsm/L, at most 450 mOsm/L, or at most 500 mOsm/L. In still other aspects of this embodiment, a hydrogel composition exhibits an osmolarity of, e.g., about 100 mOsm/L to about 500 mOsm/L, about 200 mOsm/L to about 500 mOsm/L, about 200 mOsm/L to about 400 mOsm/L, about 300 mOsm/L to about 400 mOsm/L, about 270 mOsm/L to about 390 mOsm/L, about 225 mOsm/L to about 350 mOsm/L, about 250 mOsm/L to about 325 mOsm/L, about 275 mOsm/L to about 300 mOsm/L, or about 285 mOsm/L to about 290 mOsm/L.

Aspects of the present specification provide, in part, a hydrogel composition disclosed herein that exhibits a physiologically-acceptable osmolality. As used herein, the term "osmolality" refers to the concentration of osmotically active solutes per kilo of solvent in the body. As used herein, the term "a physiologically-acceptable osmolality" refers to an osmolality in accord with, or characteristic of, the normal functioning of a living organism. As such, administration of a hydrogel composition disclosed herein exhibits an osmolality that has substantially no long term or permanent detrimental effect when administered to a mammal. Osmolality is expressed in terms of osmoles of osmotically active solute per kilogram of solvent (osmol/kg or Osm/kg) and is equal to the sum of the molalities of all the solutes present in that solution. The osmolality of a solution can be measured using an osmometer. The most commonly used instrument in modern laboratories is a freezing point depression osmometer. This instruments measure the change in freezing point that occurs in a solution with increasing osmolality (freezing point depression osmometer) or the change in vapor pressure that occurs in a solution with increasing osmolality (vapor pressure depression osmometer).

In an embodiment, a hydrogel composition disclosed herein exhibits a physiologically-acceptable osmolality. In aspects of this embodiment, a hydrogel composition exhibits an osmolality of, e.g., about 100 mOsm/kg, about 150 mOsm/kg, about 200 mOsm/kg, about 250 mOsm/kg, about 300 mOsm/kg, about 350 mOsm/kg, about 400 mOsm/kg, about 450 mOsm/kg, or about 500 mOsm/kg. In other aspects of this embodiment, a hydrogel composition exhibits an osmolality of, e.g., at least 100 mOsm/kg, at least 150 mOsm/kg, at least 200 mOsm/kg, at least 250 mOsm/kg, at least 300 mOsm/kg, at least 350 mOsm/kg, at least 400 mOsm/kg, at least 450 mOsm/kg, or at least 500 mOsm/kg. In yet other aspects of this embodiment, a hydrogel composition exhibits an osmolality of, e.g., at most 100 mOsm/kg, at most 150 mOsm/kg, at most 200 mOsm/kg, at most 250 mOsm/kg, at most 300 mOsm/kg, at most 350 mOsm/kg, at most 400 mOsm/kg, at most 450 mOsm/kg, or at most 500 mOsm/kg. In still other aspects of this embodiment, a hydrogel composition exhibits an osmolality of, e.g., about 100 mOsm/kg to about 500 mOsm/kg, about 200 mOsm/kg to about 500 mOsm/kg, about 200 mOsm/kg to about 400 mOsm/kg, about 300 mOsm/kg to about 400 mOsm/kg, about 270 mOsm/kg to about 390 mOsm/kg, about 225 mOsm/kg to about 350 mOsm/kg, about 250 mOsm/kg to about 325 mOsm/kg, about 275 mOsm/kg to about 300 mOsm/kg, or about 285 mOsm/kg to about 290 mOsm/kg.

Aspects of the present specification provide, in part, a hydrogel composition disclosed herein that exhibits substantial stability. As used herein, the term "stability" or "stable" when referring to a hydrogel composition disclosed herein refers to a composition that is not prone to degrading, decomposing, or breaking down to any substantial or significant degree while stored before administration to an individual. As used herein, the term "substantial heat stability", "substantially heat stable", "autoclave stable", or "steam sterilization stable" refers to a hydrogel composition disclosed herein that is substantially stable when subjected to a heat treatment as disclosed herein.

Stability of a hydrogel composition disclosed herein can be determined by subjecting a hydrogel composition to a heat treatment, such as, e.g., steam sterilization at normal pressure or under pressure (e.g., autoclaving). Preferably the heat treatment is carried out at a temperature of at least about 100° C. for between about one minute and about 15 minutes. Substantial stability of a hydrogel composition disclosed herein can be evaluated 1) by determining the change in the extrusion force (ΔF) of a hydrogel composition disclosed herein after sterilization, where the change in extrusion force less 2N is indicative of a substantially stable hydrogel composition as measured by (the extrusion force of a hydrogel composition with the specified additives) minus (the extrusion force of the a hydrogel composition without the added additives); and/or 2) by determining the change in rheological properties of a hydrogel composition disclosed herein after sterilization, where the change in tan δ 1 Hz of less than 0.1 is indicative of a substantially stable hydrogel composition as measured by Δ Tan δ 1 Hz=(tan δ 1 Hz of gel formulation with additives) minus (tan δ 1 Hz of gel formulation without additives). As such, a substantially stable hydrogel composition disclosed herein retains one or more of the following characteristics after sterilization: homogeneousness, extrusion force, cohesiveness, hyaluronan concentration, agent(s) concentration, osmolarity, pH, or other rheological characteristics such as tan δ.

In an aspect of this embodiment, when the change in rheological properties becomes negative (ie. tan δ lower after sterilization with the additive), the formulation is said to be more stable over sterilization due to the antioxidant.

In an embodiment, a hydrogel composition comprising a glycosaminoglycan polymer and the at least one agent disclosed herein is processed using a heat treatment that maintains the desired hydrogel properties disclosed herein. In aspects of this embodiment, a hydrogel composition comprising a glycosaminoglycan polymer and the at least one agent disclosed herein is processed using a heat treatment of, e.g., about 100° C., about 105° C., about 110° C., about 115° C., about 120° C., about 125° C., or about 130° C. In other aspects of this embodiment, a hydrogel composition comprising a glycosaminoglycan polymer and the at least one agent disclosed herein is processed using a heat treatment of, e.g., at least 100° C., at least 105° C., at least 110° C., at least 115° C., at least 120° C., at least 125° C., or at least 130° C. In yet other aspects of this embodiment, a hydrogel composition comprising a glycosaminoglycan polymer and the at least one agent disclosed herein is processed using a heat treatment of, e.g., about 100° C. to about 120° C., about 100° C. to about 125° C., about 100° C. to about 130° C., about 100° C. to about 135° C., about 110° C. to about 120° C., about 110° C. to about 125° C., about 110° C. to about 130° C., about 110° C. to about 135° C., about 120° C. to about 125° C., about 120° C. to about 130° C., about 120° C. to about 135° C., about 125° C. to about 130° C., or about 125° C. to about 135° C.

Long term stability of a hydrogel composition disclosed herein can be determined by subjecting a hydrogel composition to a heat treatment, such as, e.g., storage in an about 45° C. environment for about 60 days. Long term stability of a hydrogel composition disclosed herein can be evaluated 1) by assessing the clarity and color of a hydrogel composition after the 45° C. heat treatment, with a clear and uncolored hydrogel composition being indicative of a substantially stable hydrogel composition; 2) by determining the change in the extrusion force (ΔF) of a hydrogel composition disclosed herein after the 45° C. heat treatment, where the change in extrusion force less 2N is indicative of a substantially stable hydrogel composition as measured by (the extrusion force of a hydrogel composition with the specified additives before and after the 45° C. heat treatment) minus (the extrusion force of the a hydrogel composition without the specified additives before and after the 45° C. heat treatment); and 3) by determining the change in rheological properties of a hydrogel composition disclosed herein after sterilization, where the change in tan δ 1 Hz of less than 0.1 is indicative of a substantially stable hydrogel composition as measured by Δ Tan δ 1 Hz=(tan δ 1 Hz of gel formulation with the specified additives before and after the 45° C. heat treatment) minus (tan δ 1 Hz of gel formulation without the specified additives before and after the 45° C. heat treatment). As such, a long term stability of a hydrogel composition disclosed herein is evaluated by retention of one or more of the following characteristics after the 45° C. heat treatment: clarity (transparency and translucency), homogeneousness, and cohesiveness.

In aspects of this embodiment, when Δ Tan δ 1 Hz becomes negative over sterilization, the formulation with the antioxidant is more stable over sterilization.

In aspects of this embodiment, a hydrogel composition is substantially stable at room temperature for, e.g., about 3 months, about 6 months, about 9 months, about 12 months, about 15 months, about 18 months, about 21 months, about 24 months, about 27 months, about 30 months, about 33 months, or about 36 months. In other aspects of this embodiment, a hydrogel composition is substantially stable at room temperature for, e.g., at least 3 months, at least 6 months, at least 9 months, at least 12 months, at least 15 months, at least 18 months, at least 21 months, at least 24 months, at least 27 months, at least 30 months, at least 33 months, or at least 36 months. In other aspects of this embodiment, a hydrogel composition is substantially stable at room temperature for, e.g., about 3 months to about 12 months, about 3 months to about 18 months, about 3 months to about 24 months, about 3 months to about 30 months, about 3 months to about 36 months, about 6 months to about 12 months, about 6 months to about 18 months, about 6 months to about 24 months, about 6 months to about 30 months, about 6 months to about 36 months, about 9 months to about 12 months, about 9 months to about 18 months, about 9 months to about 24 months, about 9 months to about 30 months, about 9 months to about 36 months, about 12 months to about 18 months, about 12 months to about 24 months, about 12 months to about 30 months, about 12 months to about 36 months, about 18 months to about 24 months, about 18 months to about 30 months, or about 18 months to about 36 months.

In aspects of this embodiment, the resistance of formulations to degradation by free radicals can be assessed to characterize the effect of the antioxidant. Degradation by free radicals was simulated on a rheometer (Haake Rheostress 600) by addition of 1/7 ratio of $H_2O_2$ 30% on the surface of a spread gel measured with a controlled stress rheometer according to the following method: frequency of 1 Hz with 0.8% controlled strain, during 3600 seconds at 35° C. The complex viscosity or elastic modulus decrease is followed versus time and the value of the slope to characterizes the speed of free radical degradation. The time it takes for complex viscosity or elastic modulus to decrease by 70% is called $T_{30}$. Comparing T30 with and without the antioxidant is a measurement of potential duration.

Aspects of the present specification provide, in part, a method of treating a soft tissue condition of an individual by administering a hydrogel composition disclosed herein. As used herein, the term "treating," refers to reducing or eliminating in an individual a cosmetic or clinical symptom of a soft tissue condition characterized by a soft tissue imperfection, defect, disease, and/or disorder; or delaying or preventing in an individual the onset of a cosmetic or clinical symptom of a condition characterized by a soft tissue imperfection, defect, disease, and/or disorder. For example, the term "treating" can mean reducing a symptom of a condition characterized by a soft tissue defect, disease, and/or disorder by, e.g., at least 20%, at least 30%, at least 40%, at least 50%, at least 60%, at least 70%, at least 80%, at least 90% or at least 100%. The effectiveness of a hydrogel composition disclosed herein in treating a condition characterized by a soft tissue defect, disease, and/or disorder can be determined by observing one or more cosmetic, clinical symptoms, and/or physiological indicators associated with the condition. An improvement in a soft tissue defect, disease, and/or disorder also can be indicated by a reduced need for a concurrent therapy. Those of skill in the art will know the appropriate symptoms or indicators associated with specific soft tissue defect, disease, and/or disorder and will know how to determine if an individual is a candidate for treatment with a compound or composition disclosed herein.

A hydrogel composition is administered to an individual. An individual is typically a human being of any age, gender or race. Typically, any individual who is a candidate for a conventional procedure to treat a soft tissue condition is a candidate for a method disclosed herein. Although a subject experiencing the signs of aging skin is an adult, subjects experiencing premature aging or other skin conditions suitable for treatment (for example, a scar) can also be treated with a hydrogel composition disclosed herein. In addition, the presently disclosed hydrogel compositions and methods may apply to individuals seeking a small/moderate enlargement, shape change or contour alteration of a body part or region, which may not be technically possible or aesthetically acceptable with existing soft tissue implant technology. Pre-operative evaluation typically includes routine history and physical examination in addition to thorough informed consent disclosing all relevant risks and benefits of the procedure.

The hydrogel composition and methods disclosed herein are useful in treating a soft tissue condition. A soft tissue condition includes, without limitation, a soft tissue imperfection, defect, disease, and/or disorder. Non-limiting examples of a soft tissue condition include breast imperfection, defect, disease and/or disorder, such as, e.g., a breast augmentation, a breast reconstruction, mastopexy, micromastia, thoracic hypoplasia, Poland's syndrome, defects due to implant complications like capsular contraction and/or rupture; a facial imperfection, defect, disease or disorder, such as, e.g., a facial augmentation, a facial reconstruction, a mesotherapy, Parry-Romberg syndrome, lupus erythematosus profundus, dermal divots, scars, sunken cheeks, thin lips, nasal imperfections or defects, retro-orbital imperfections or defects, a facial fold, line and/or wrinkle like a glabellar line, a nasolabial line, a perioral line, and/or a marionette line, and/or other contour deformities or imperfections of the face; a neck imperfection, defect, disease or disorder; a skin imperfection, defect, disease and/or disorder; other soft tissue imperfections, defects, diseases and/or disorders, such as, e.g., an augmentation or a reconstruction of the upper arm, lower arm, hand, shoulder, back, torso including abdomen, buttocks, upper leg, lower leg including calves, foot including plantar fat pad, eye, genitals, or other body part, region or area, or a disease or disorder affecting these body parts, regions or areas; urinary incontinence, fecal incontinence, other forms of incontinence; and gastroesophageal reflux disease (GERD). As used herein, the term "mesotherapy" refers to a non-surgical cosmetic treatment technique of the skin involving intra-epidermal, intradermal, and/or subcutaneous injection of an agent administered as small multiple droplets into the epidermis, dermoepidermal junction, and/or the dermis.

The amount of a hydrogel composition used with any of the methods as disclosed herein will typically be determined based on the alteration and/or improvement desired, the reduction and/or elimination of a soft tissue condition symptom desired, the clinical and/or cosmetic effect desired by the individual and/or physician, and the body part or region being treated. The effectiveness of composition administration may be manifested by one or more of the following clinical and/or cosmetic measures: altered and/or improved soft tissue shape, altered and/or improved soft tissue size, altered and/or improved soft tissue contour, altered and/or improved tissue function, tissue ingrowth support and/or new collagen deposition, sustained engraftment of composition, improved patient satisfaction and/or quality of life, and decreased use of implantable foreign material.

For example, for breast augmentation procedures, effectiveness of the compositions and methods may be manifested by one or more of the following clinical and/or cosmetic measures: increased breast size, altered breast shape, altered breast contour, sustained engraftment, reduction in the risk of capsular contraction, decreased rate of liponecrotic cyst formation, improved patient satisfaction and/or quality of life, and decreased use of breast implant.

As another example, effectiveness of the compositions and methods in treating a facial soft tissue may be manifested by one or more of the following clinical and/or cosmetic measures: increased size, shape, and/or contour of facial feature like increased size, shape, and/or contour of lip, cheek or eye region; altered size, shape, and/or contour of facial feature like altered size, shape, and/or contour of lip, cheek or eye region shape; reduction or elimination of a wrinkle, fold or line in the skin; resistance to a wrinkle, fold or line in the skin; rehydration of the skin; increased elasticity to the skin; reduction or elimination of skin roughness; increased and/or improved skin tautness; reduction or elimination of stretch lines or marks; increased and/or improved skin tone, shine, brightness and/or radiance; increased and/or improved skin color, reduction or elimination of skin paleness; sustained engraftment of composition; decreased side effects; improved patient satisfaction and/or quality of life.

As yet another example, for urinary incontinence procedures, effectiveness of the compositions and methods for sphincter support may be manifested by one or more of the following clinical measures: decreased frequency of incontinence, sustained engraftment, improved patient satisfaction and/or quality of life, and decreased use of implantable foreign filler.

In aspects of this embodiment, the amount of a hydrogel composition administered is, e.g., about 0.01 g, about 0.05 g, about 0.1 g, about 0.5 g, about 1 g, about 5 g, about 10 g, about 20 g, about 30 g, about 40 g, about 50 g, about 60 g, about 70 g, about 80 g, about 90 g, about 100 g, about 150 g, or about 200 g. In other aspects of this embodiment, the amount of a hydrogel composition administered is, e.g., about 0.01 g to about 0.1 g, about 0.1 g to about 1 g, about 1 g to about 10 g, about 10 g to about 100 g, or about 50 g to about 200 g. In yet other aspects of this embodiment, the amount of a hydrogel composition administered is, e.g., about 0.01 mL, about 0.05 mL, about 0.1 mL, about 0.5 mL, about 1 mL, about 5 mL, about 10 mL, about 20 mL, about 30 mL, about 40 mL, about 50 mL, about 60 mL, about 70 g, about 80 mL, about 90 mL, about 100 mL, about 150 mL, or about 200 mL. In other aspects of this embodiment, the amount of a hydrogel composition administered is, e.g., about 0.01 mL to about 0.1 mL, about 0.1 mL to about 1 mL, about 1 mL to about 10 mL, about 10 mL to about 100 mL, or about 50 mL to about 200 mL.

The duration of treatment will typically be determined based on the cosmetic and/or clinical effect desired by the individual and/or physician and the body part or region being treated. In aspects of this embodiment, administration of a hydrogel composition disclosed herein can treat a soft tissue condition for, e.g., about 6 months, about 7 months, about 8 months, about 9 months, about 10 months, about 11 months, about 12 months, about 13 months, about 14 months, about 15 months, about 18 months, or about 24 months. In other aspects of this embodiment, administration of a hydrogel composition disclosed herein can treat a soft tissue condition for, e.g., at least 6 months, at least 7 months, at least 8 months, at least 9 months, at least 10 months, at least 11 months, at least 12 months, at least 13 months, at least 14 months, at least 15 months, at least 18 months, or at least 24 months. In yet aspects of this embodiment, administration of a hydrogel composition disclosed herein can treat a soft tissue condition for, e.g., about 6 months to about 12 months, about 6 months to about 15 months, about 6 months to about 18 months, about 6 months to about 21 months, about 6 months to about 24 months, about 9 months to about 12 months, about 9 months to about 15 months, about 9 months to about 18 months, about 9 months to about 21 months, about 6 months to about 24 months, about 12 months to about 15 months, about 12 months to about 18 months, about 12 months to about 21 months, about 12 months to about 24 months, about 15 months to about 18 months, about 15 months to about 21 months, about 15 months to about 24 months, about 18 months to about 21 months, about 18 months to about 24 months, or about 21 months to about 24 months.

Aspects of the present specification provide, in part, administering a hydrogel composition disclosed herein. As used herein, the term "administering" means any delivery mechanism that provides a composition disclosed herein to an individual that potentially results in a clinically, therapeutically, or experimentally beneficial result. The actual delivery mechanism used to administer a composition to an individual can be determined by a person of ordinary skill in the art by taking into account factors, including, without limitation, the type of skin condition, the location of the skin condition, the cause of the skin condition, the severity of the skin condition, the degree of relief desired, the duration of relief desired, the particular composition used, the rate of excretion of the particular composition used, the pharmacodynamics of the particular composition used, the nature of the other compounds included in the particular composition used, the particular route of administration, the particular characteristics, history and risk factors of the individual, such as, e.g., age, weight, general health and the like, or any combination thereof. In an aspect of this embodiment, a composition disclosed herein is administered to a skin region of an individual by injection.

The route of administration of a hydrogel composition to an individual patient will typically be determined based on the cosmetic and/or clinical effect desired by the individual and/or physician and the body part or region being treated. A composition disclosed herein may be administered by any means known to persons of ordinary skill in the art including, without limitation, syringe with needle, a pistol (for example, a hydropneumatic-compression pistol), catheter, topically, or by direct surgical implantation. The hydrogel composition disclosed herein can be administered into a skin region such as, e.g., a dermal region or a hypodermal region.

For example, a hydrogel composition disclosed herein can be injected utilizing needles with a diameter of about 0.26 mm to about 0.4 mm and a length ranging from about 4 mm to about 14 mm. Alternately, the needles can be 21 to 32 G and have a length of about 4 mm to about 70 mm. Preferably, the needle is a single-use needle. The needle can be combined with a syringe, catheter, and/or a pistol.

In addition, a composition disclosed herein can be administered once, or over a plurality of times. Ultimately, the timing used will follow quality care standards. For example, a hydrogel composition disclosed herein can be administered once or over several sessions with the sessions spaced apart by a few days, or weeks. For instance, an individual can be administered a hydrogel composition disclosed herein every 1, 2, 3, 4, 5, 6, or 7 days or every 1, 2, 3, or 4 weeks. The administration a hydrogel composition disclosed herein to an individual can be on a monthly or bi-monthly basis or administered every 3, 6, 9, or 12 months.

For a breast soft tissue replacement procedure, the route of administration may include axillary, periareolar, and/or inframammary routes. Alternatively or in addition, a composition may be delivered through a transaxillary endoscopic subpectoral approach. For a facial soft tissue replacement procedure, the route of administration can be frontal, temporal, zygomatic, periocular, mandibula, perioral or chin routes. In urinary incontinence procedures, the route of administration may include transurethral or periurethral routes. Alternatively or in addition, administration may be delivered via an antegrade route. The routes discussed herein do not exclude the use of multiple routes to achieve the desired clinical effect.

Aspects of the present specification provide, in party a dermal region. As used herein, the term "dermal region" refers to the region of skin comprising the epidermal-dermal junction and the dermis including the superficial dermis (papillary region) and the deep dermis (reticular region). The skin is composed of three primary layers: the epidermis, which provides waterproofing and serves as a barrier to infection; the dermis, which serves as a location for the appendages of skin; and the hypodermis (subcutaneous adipose layer). The epidermis contains no blood vessels, and is nourished by diffusion from the dermis. The main type of cells which make up the epidermis are keratinocytes, melanocytes, Langerhans cells and Merkels cells.

The dermis is the layer of skin beneath the epidermis that consists of connective tissue and cushions the body from stress and strain. The dermis is tightly connected to the epidermis by a basement membrane. It also harbors many Mechanoreceptor/nerve endings that provide the sense of touch and heat. It contains the hair follicles, sweat glands, sebaceous glands, apocrine glands, lymphatic vessels and blood vessels. The blood vessels in the dermis provide nourishment and waste removal from its own cells as well as from the Stratum basale of the epidermis. The dermis is structurally divided into two areas: a superficial area adjacent to the epidermis, called the papillary region, and a deep thicker area known as the reticular region.

The papillary region is composed of loose areolar connective tissue. It is named for its fingerlike projections called papillae that extend toward the epidermis. The papillae provide the dermis with a "bumpy" surface that interdigitates with the epidermis, strengthening the connection between the two layers of skin. The reticular region lies deep in the papillary region and is usually much thicker. It is composed of dense irregular connective tissue, and receives its name from the dense concentration of collagenous, elastic, and reticular fibers that weave throughout it. These protein fibers give the dermis its properties of strength, extensibility, and elasticity. Also located within the reticular region are the roots of the hair, sebaceous glands, sweat glands, receptors, nails, and blood vessels. Tattoo ink is held in the dermis. Stretch marks from pregnancy are also located in the dermis.

The hypodermis lies below the dermis. Its purpose is to attach the dermal region of the skin to underlying bone and muscle as well as supplying it with blood vessels and nerves. It consists of loose connective tissue and elastin. The main cell types are fibroblasts, macrophages and adipocytes (the hypodermis contains 50% of body fat). Fat serves as padding and insulation for the body.

In an aspect of this embodiment, a hydrogel composition disclosed herein is administered to a skin region of an individual by injection into a dermal region or a hypodermal region. In aspects of this embodiment, a hydrogel composition disclosed herein is administered to a dermal region of an individual by injection into, e.g., an epidermal-dermal junction region, a papillary region, a reticular region, or any combination thereof.

Aspects of the present specification disclose, in part, a method of treating a soft tissue condition of an individual, the method comprising the steps of administering a hydrogel composition disclosed herein to a site of the soft tissue condition of the individual, wherein the administration of the composition improves the soft tissue condition, thereby treating the soft tissue condition. In aspects of this embodiment, a soft tissue, condition is a breast tissue condition, a facial tissue condition, a neck condition, a skin condition, an upper arm condition, a lower arm condition, a hand condition, a shoulder condition, a back condition, a torso including abdominal condition, a buttock condition, an upper leg condition, a lower leg condition including calf condition, a foot condition including plantar fat pad condition, an eye condition, a genital condition, or a condition effecting another body part, region or area.

Other aspects of the present specification disclose, in part, a method of treating a skin condition comprises the step of administering to an individual suffering from a skin condition a hydrogel composition disclosed herein, wherein the administration of the composition improves the skin condition, thereby treating the skin condition. In an aspect of this embodiment, a skin condition is a method of treating skin dehydration comprises the step of administering to an individual suffering from skin dehydration a hydrogel composition disclosed herein, wherein the administration of the composition rehydrates the skin, thereby treating skin dehydration. In another aspect of this embodiment, a method of treating a lack of skin elasticity comprises the step of administering to an individual suffering from a lack of skin elasticity a hydrogel composition disclosed herein, wherein the administration of the composition increases the elasticity of the skin, thereby treating a lack of skin elasticity. In yet another aspect of this embodiment, a method of treating skin roughness comprises the step of administering to an individual suffering from skin roughness a hydrogel composition disclosed herein, wherein the administration of the composition decreases skin roughness, thereby treating skin roughness. In still another aspect of this embodiment, a method of treating a lack of skin tautness comprises the step of administering to an individual suffering from a lack of skin tautness a hydrogel composition disclosed herein, wherein the administration of the composition makes the skin tauter, thereby treating a lack of skin tautness.

In a further aspect of this embodiment, a method of treating a skin stretch line or mark comprises the step of administering to an individual suffering from a skin stretch line or mark a hydrogel composition disclosed herein, wherein the administration of the composition reduces or eliminates the skin stretch line or mark, thereby treating a skin stretch line or mark. In another aspect of this embodiment, a method of treating skin paleness comprises the step of administering to an individual suffering from skin paleness a hydrogel composition disclosed herein, wherein the administration of the composition increases skin tone or radiance, thereby treating skin paleness. In another aspect of this embodiment, a method of treating skin wrinkles comprises the step of administering to an individual suffering from skin wrinkles a hydrogel composition disclosed herein, wherein the administration of the composition reduces or eliminates skin wrinkles, thereby treating skin wrinkles. In yet another aspect of this embodiment, a method of treating skin wrinkles comprises the step of administering to an individual a hydrogel composition disclosed herein, wherein the administration of the composition makes the skin resistant to skin wrinkles, thereby treating skin wrinkles.

EXAMPLES

The following examples illustrate representative embodiments now contemplated, but should not be construed to limit the disclosed hydrogel compositions, and methods of soft tissue augmentation using such hydrogel compositions.

Reminder for stability assessment with extrusion force: $\Delta F$ (F gel with additive −F gel without additive)<2N
Reminder for stability assessment with rheology: $\Delta \tan \delta$ ($\tan \delta$ 1 Hz gel with additive −$\tan \delta$ 1 Hz gel without additive)<0.1

Example 1

Effect of Caffeic Acid Agent on HA-Based Gel Formulation Incorporation and Autoclaving Stability Caffeic acid, at a concentration of 0.6%,(w/w), was incorporated into a HA-based gel matrix at 24 mg/g containing 5% of uncrosslinked HA. The gel formulated was autoclaved. The gel obtained before autoclaving was clear and brown, the gel obtained after autoclaving was similar.

Rheological and extrusion force properties of the gel were analyzed and determined as shown below in Table 2:

TABLE 2

Physical properties before and after autoclaving.

| Before autoclaving | | | After autoclaving | | |
| --- | --- | --- | --- | --- | --- |
| $\Delta$pH | $\Delta$F(N) | $\Delta \tan \delta$ (1 Hz) | $\Delta$pH | $\Delta$F(N) | $\Delta \tan \delta$ (1 Hz) |
| 0.18 | 0.2 | −0.003 | 0.55 | 2.9 | 0.02 |

Extrusion analysis showed the beginning of degradation of the uncrosslinked hyaluronic acid.

Example 2

Effect of Caffeic Acid Agent on HA-Based Gel Formulation Long Term Stability

The formulations prepared in Example 1 were tested for stability at 45° C. for 60 days and compared to a HA-based gel matrix without any added additives. After 30 days at 45° C., the gel became dark brown, and physical analysis of the gel showed a degradation of the formulation as shown by the values contained in Table 3 below.

TABLE 3

| Physical properties over time. | | | | | | | | |
|---|---|---|---|---|---|---|---|---|
| 10 days at 45° C. | | | 20 days at 45° C. | | | 30 days at 45° C. | | |
| ΔpH | ΔF (N) | ΔTan δ (1 Hz) | ΔpH | Δ F (N) | ΔTan δ (1 Hz) | ΔpH | ΔF (N) | ΔTan δ (1 Hz) |
| 1.05 | 4.3 | 0.0560 | 0.90 | 4.7 | 0.077 | 1.06 | 4.9 | 0.144 |

Based on these results, it was concluded that direct incorporation of caffeic acid in the gel leads to the degradation of the final product.

Example 3

Effect of Inoveol CAFA Agent on HA-Based Gel Formulation Incorporation and Autoclaving Stability Inoveol® CAFA (supplied by Libragen), (INCI name: Aqua (and) Caffeyl Glucoside), a derivative of caffeic acid, at a concentration of 0.5% (w/w) of commercial solution, was incorporated into a HA-based gel matrix containing a viscoelastic portion. The gel formulated was autoclaved. The gel obtained before autoclaving was clear and slightly yellow, the gel obtained after autoclaving was similar.

Rheological and extrusion force properties of the gel were analyzed and are summarized in Table 4 below.

TABLE 4

| Physical properties before and after autoclaving. | | | | | |
|---|---|---|---|---|---|
| Before autoclaving | | | After autoclaving | | |
| ΔpH | ΔF(N) | ΔTan δ | ΔpH | ΔF(N) | ΔTan δ |
| −0.23 | 0.8 | 0.01 | −0.18 | 1.6 | 0.02 |

Based on the above results, it was concluded that the gel with Inoveol® CAFA was stable after autoclaving, as opposed to the same gel with caffeic acid.

Example 4

Effect of Inoveol® CAFA Agent on HA-Based Gel Formulation Long Term Stability

Figure 2:
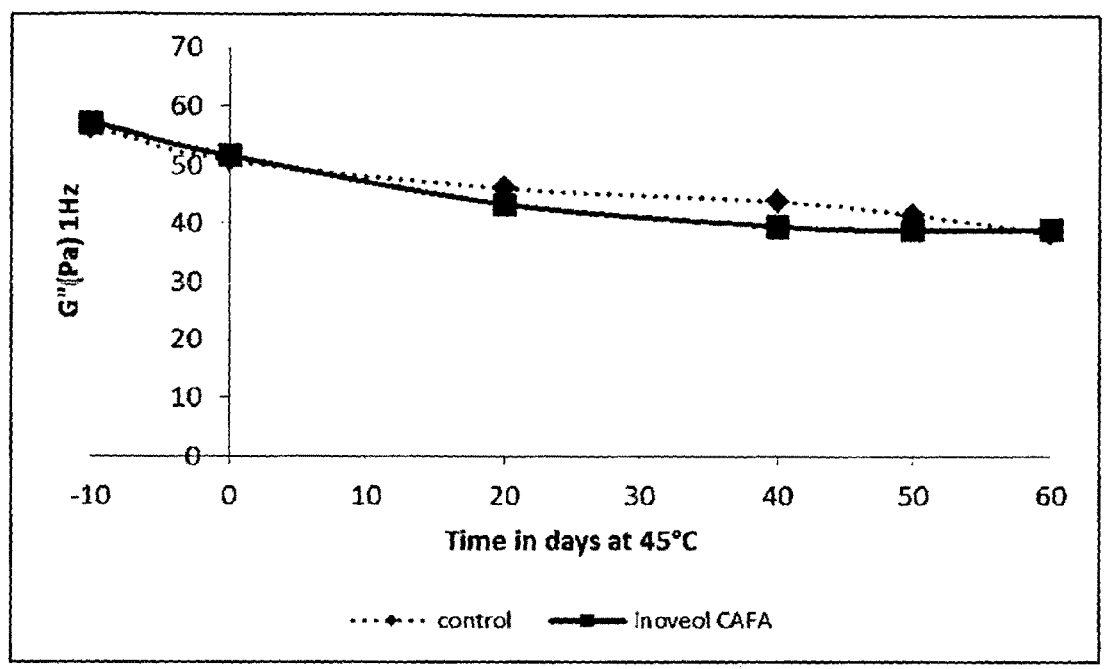
FIG. 2 is a graph illustrating experimental data obtained that demonstrates the effect of an accelerated aging at 45° C. for 60 days on the viscous modulus G" of the same gel with and without Inoveol® CAFA at 0.5% (w/w).
Figure 3:
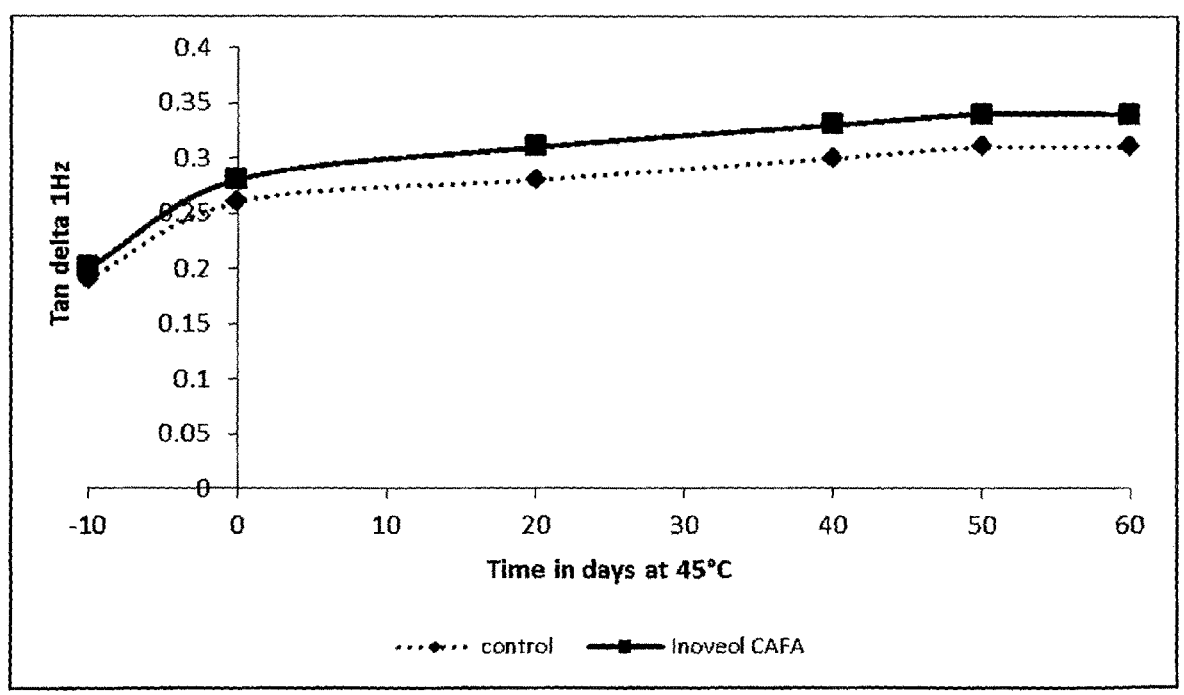
FIG. 3 is a graph illustrating experimental data obtained that demonstrates the effect of an accelerated aging at 45° C. for 60 days on the tan delta of the same gel with and without Inoveol® CAFA at 0.5% (w/w).

The formulation prepared in Example 3 was subjected to accelerated aging or accelerated degradation in order to test the stability of the gel. Specifically, the gel was tested for stability at 45° C. for 60 days and compared to a HA-based gel matrix without any added additives. The results are shown in Table 5 below. FIGS. 1-3 also illustrate experimental data obtained in this experiment that demonstrate the effect of time on the physical properties of the tested gel.

TABLE 5

| Physical properties after 60 days. 60 days at 45° C. | | |
|---|---|---|
| ΔpH | ΔF(N) | Δ Tan δ |
| −0.18 | 1.9 | 0.03 |

Based on the results of this example, it was determined that the incorporation of Inoveol CAFA in a gel did not degrade physical properties of the gel, as opposed to caffeic acid (Example 2).

Example 5

Inoveol® CAFA Protects HA-Based Gel Formulation from Oxidative Degradation

Figure 4:
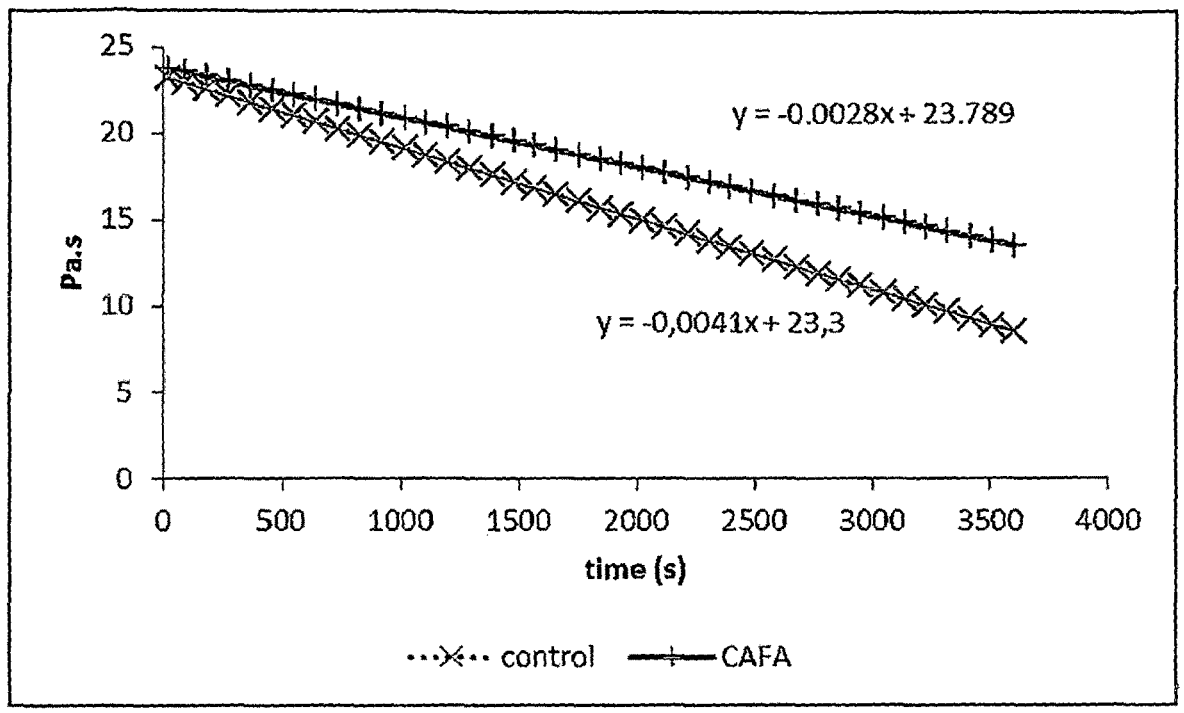
FIG. 4 is a graph illustrating experimental data obtained that demonstrates that the degradation of a gel containing 0.5% (w/w) Inoveol® CAFA, followed by its viscosity decrease over time in presence of hydrogen peroxide, is slower when compared to the same gel without Inoveol® CAFA.

The effect of Inoveol® CAFA on HA-based gel matrix oxidative degradation was studied. An oxidation test was used as it allows for a determination of the resistance of a HA-based gel matrix to free radicals. Degradation by free radicals was simulated on a rheometer (Haake Rheostress 600) by addition of 1/7 ratio of $H_2O_2$ 30% on the surface of a spread gel measured with a controlled stress rheometer according to the following method: frequency of 1 Hz with 0.8% controlled strain, during 3600 seconds at 35° C. The value of the slope characterizes the speed of free radical degradation. The results of the oxidation test are illustrated in FIG. 4. A comparison of antioxidant properties after autoclaving for a HA-based gel matrix with 0.5% (w/w) Inoveol® CAFA (slope: −0.0028) versus the same HA-based gel matrix (slope: −0.0041) showed that the gel containing Inoveol® CAFA is more stable with respect to free radical degradation. $T_{30}$ for the HA-based gel matrix with 0.5% (w/w) Inoveol® CAFA is about 5947 seconds versus 3978 seconds for the HA-based gel matrix alone. This is about a 49% improvement due to the additive.

Figure 5:
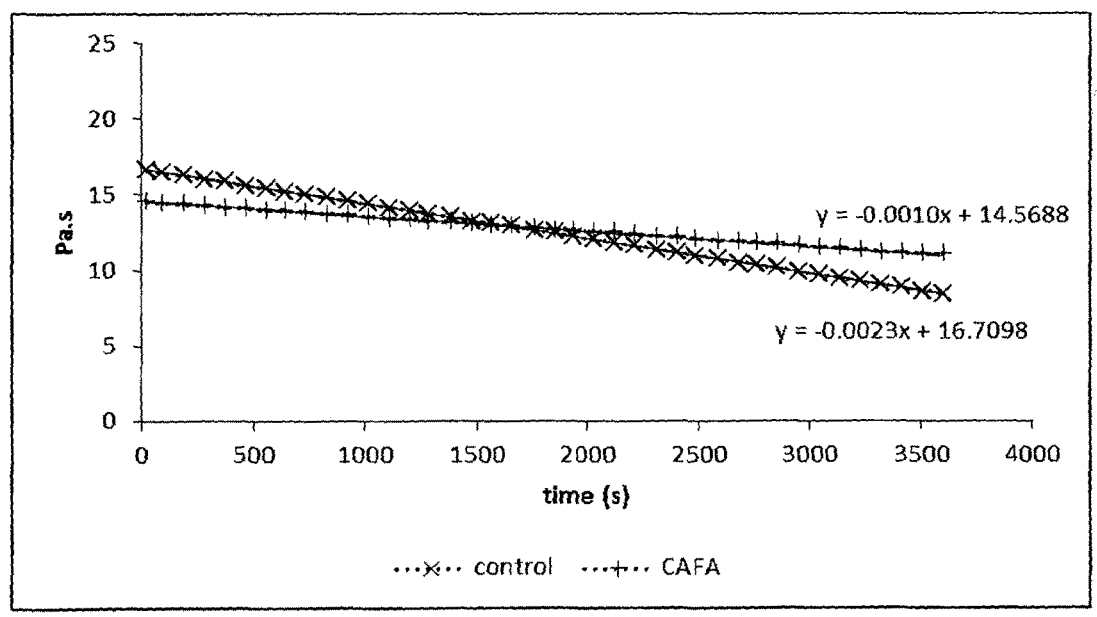
FIG. 5 is a graph illustrating experimental data obtained that demonstrates showed that the gel containing Inoveol® CAFA is still more stable with respect to free radical degradation (ratio of 1.5) after 60 days of accelerated aging at 45° C.

A comparison of antioxidant properties after thermal stability at 45° C. for 60 days for a HA-based gel matrix with 0.5% (w/w) Inoveol® CAFA (slope: −0.0010) versus the same HA-based gel matrix (slope: −0.0023) showed that the gel containing Inoveol® CAFA is more stable with respect to free radical degradation. $T_{30}$ for the HA-based gel matrix with 0.5% (w/w) Inoveol® CAFA is about 10198 seconds versus 5085 seconds for the HA-based gel matrix alone. This is a 100% improvement due to the additive. These results are illustrated in FIG. 5.

Example 6

Effect of Catechin Agent on HA-Based Gel Formulation Incorporation and Autoclaving Stability Catechin, at a concentration of 0.1% of commercial solution, was incorporated into a HA-based gel matrix at 24 mg/g containing 5% of uncrosslinked HA. The gel formulated was autoclaved. The gel obtained before autoclaving was clear and slightly orange, and the gel obtained after autoclaving was clear with orange color.

Rheological and extrusion force analysis showed a degradation of the gel as summarized in Table 6 below.

TABLE 6

Physical properties before and after autoclaving.

| Before autoclaving | | | After autoclaving | | |
|---|---|---|---|---|---|
| ΔpH | ΔF(N) | ΔTan δ | ΔpH | ΔF(N) | ΔTan δ |
| −0.11 | 0 | 0.008 | −0.35 | 6.4 | 0.162 |

Example 7

Effect of Inoveol EGCG Agent on HA-Based Gel Formulation Incorporation and Autoclaving Stability Inoveol EGCG (supplied by Libragen), (INCI Name: Epigallocatechin Gallatyl Glucoside), a derivative of catechin, at a concentration of 0.5% of commercial solution, was incorporated into a HA-based gel matrix containing viscoelastic portion. The gel formulated was autoclaved. The gel obtained before autoclaving was clear and slightly yellow and the gel obtained after autoclaving was similar.

Rheological and extrusion force properties of the gel were analyzed and showed the autoclaving stability of the gel, as summarized in Table 7 below.

TABLE 7

Physical properties before and after autoclaving.

| Before autoclaving | | | After autoclaving | | |
|---|---|---|---|---|---|
| ΔpH | ΔF(N) | ΔTan δ | ΔpH | ΔF(N) | ΔTan δ |
| −0.17 | −0.1 | 0 | −0.26 | −1.0 | −0.01 |

Based on this example, it was concluded that the gel containing Inoveol EGCG is stable to autoclaving and slightly more stable with the additive than without.

Example 8

Effect of Inoveol EGCG Agent on HA-Based Gel Formulation Long Term Stability

The formulation prepared in Example 7 was tested for stability at 45° C. for 60 days and compared to a HA-based gel matrix without any added additives. The results are summarized in Table 8 below.

Figure 6:
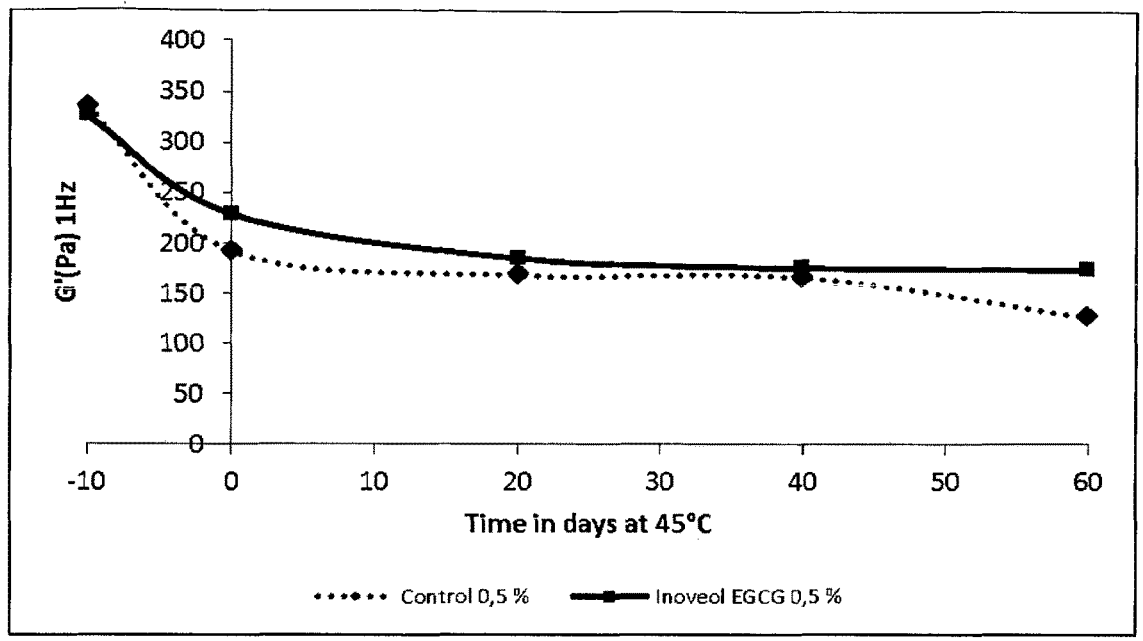
FIG. 6 is a graph illustrating experimental data obtained that demonstrates the effect of an accelerated aging at 45° C. for 60 days on the elastic modulus G' of the same gel with and without Inoveol® EGCG at 0.5% (w/w).
Figure 7:
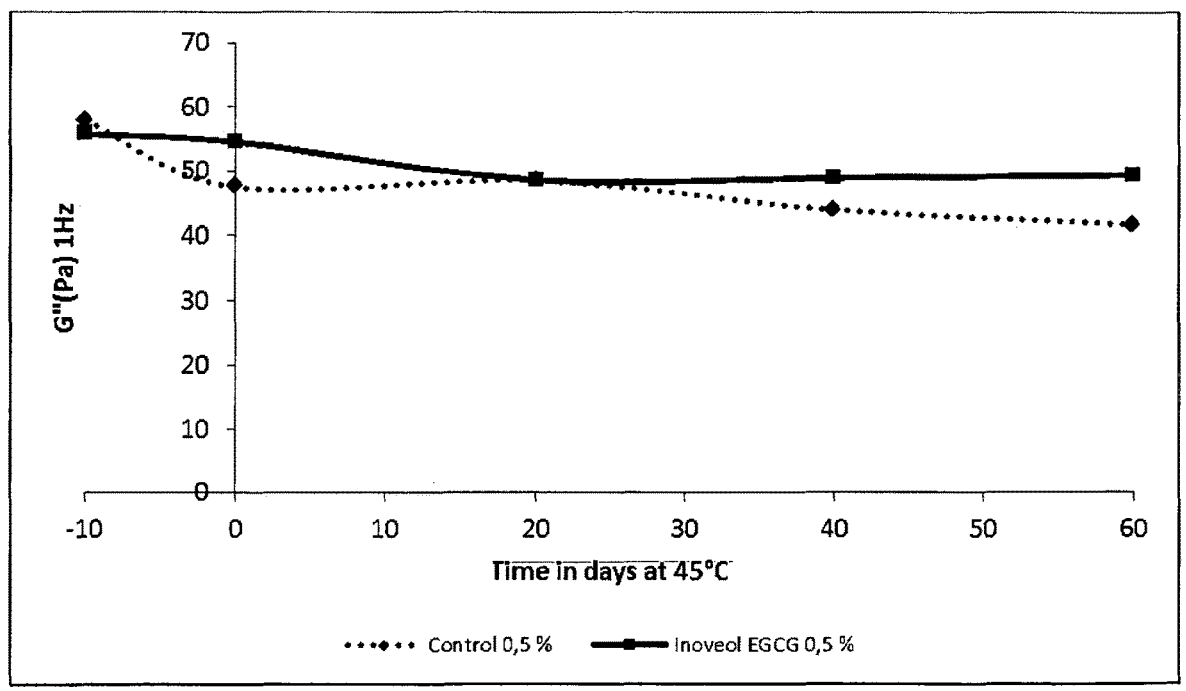
FIG. 7 is a graph that further illustrates the effect of an accelerated aging at 45° C. for 60 days on the viscous modulus G" of the same gel with and without Inoveol® EGCG at 0.5% (w/w).

Additional analysis is illustrated in FIGS. 6-7.

TABLE 8

Physical properties after 60 days.
60 days at 45° C.

| ΔpH | ΔF(N) | Δ Tan δ |
|---|---|---|
| a. −0.9 | −0.6 | −0.05 |

Figure 8:
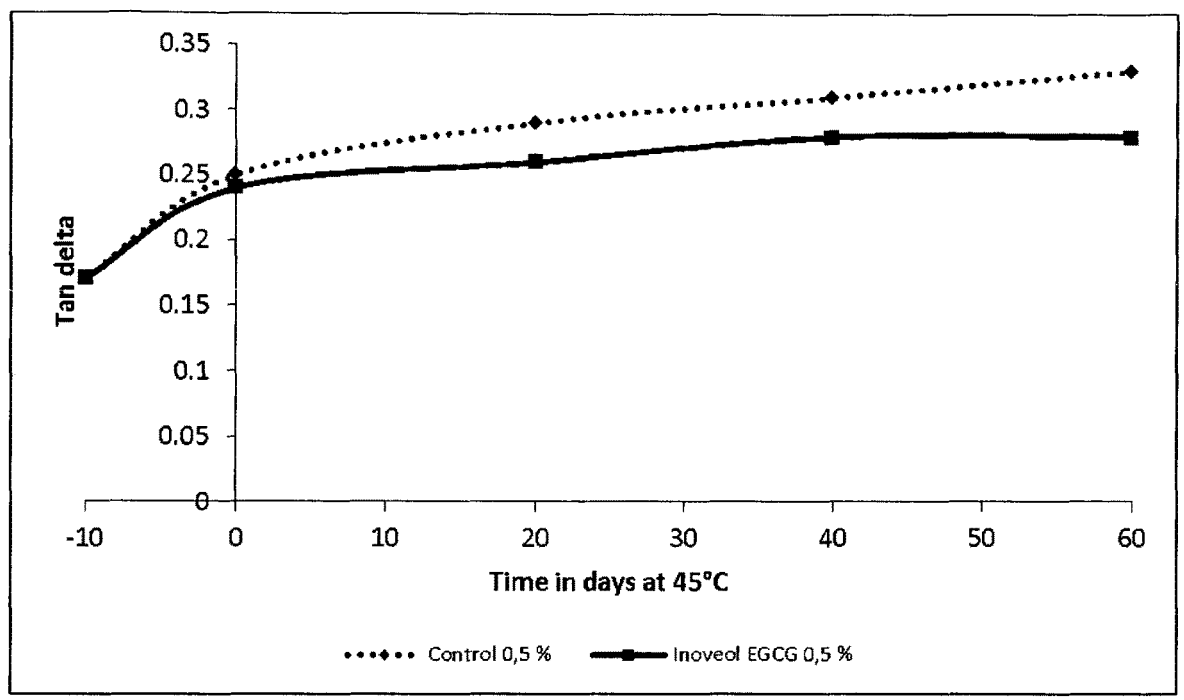
FIG. 8 is a graph that further illustrates the effect of an accelerated aging at 45° C. for 60 days on the tan delta of the same gel with and without Inoveol® EGCG at 0.5% (w/w).

Based, at least in part, on the results of this Example, it was concluded that the incorporation of Inoveol® EGCG in gel had no negative impact on the physical properties of the gel. (See FIG. 8)

Example 9

Inoveol® EGCG Protects HA-Based Gel Formulation from Oxidative Degradation

Figure 9:
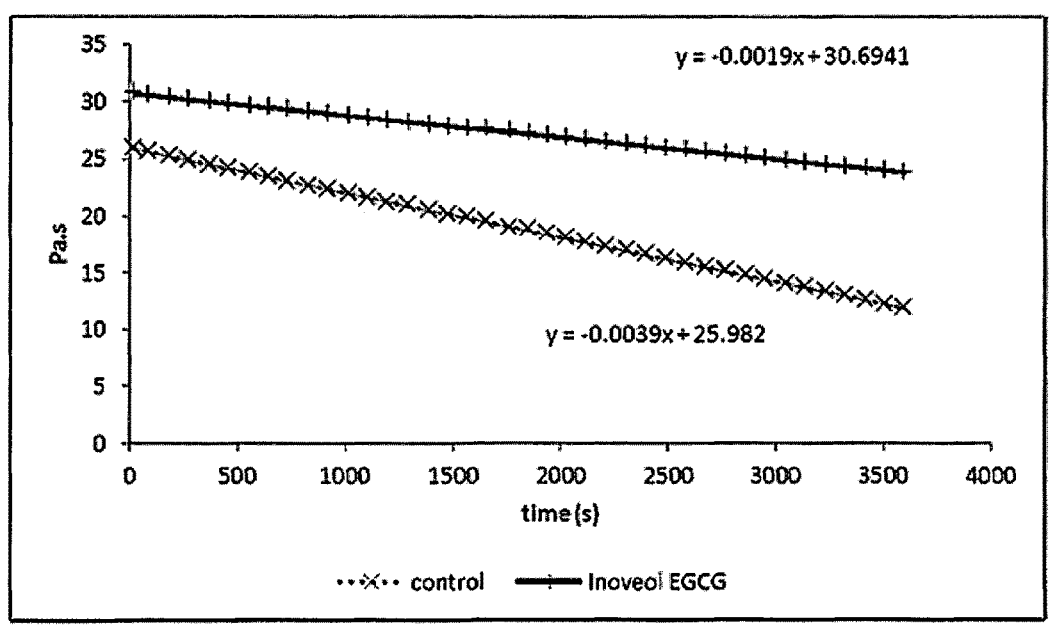
FIG. 9 is a graph illustrating experimental data obtained that demonstrates effect of Inoveol-EGCG on HA-based gel matrix oxidative degradation using hydrogen peroxide. The value of the slope characterizes the speed of free radical degradation and shows the benefit of adding Inoveol® EGCG at 0.5% (w/w).

The effect of Inoveol® EGCG on HA-based gel matrix oxidative degradation was studied. Oxidation testing was used as it allows testing of the resistance of a HA-based gel matrix to free radicals. Degradation by free radicals was simulated on a rheometer (Haake Rheostress 600) by addition of 1/7 ratio of $H_2O_2$ 30% on the surface of a spread gel measured with a controlled stress rheometer according to the following method: frequency of 1 Hz with 0.8% controlled strain, during 3600 seconds at 35° C. The value of the slope to characterizes the speed of free radical degradation. The results are illustrated in FIG. 9. A comparison of antioxidant properties after autoclaving for a HA-based gel matrix with 0.5% (w/w) Inoveol® EGCG (slope: −0.0019) versus the same HA-based gel matrix (slope: −0.0039) showed that the gel containing Inoveol EGCG is more stable with respect to free radical degradation. $T_{30}$ for the HA-based gel matrix with 0.5% (w/w) Inoveol® EGCG is about 11308 seconds versus 4663 seconds for the HA-based gel matrix alone. This is about a 142% improvement due to the additive.

Figure 10:
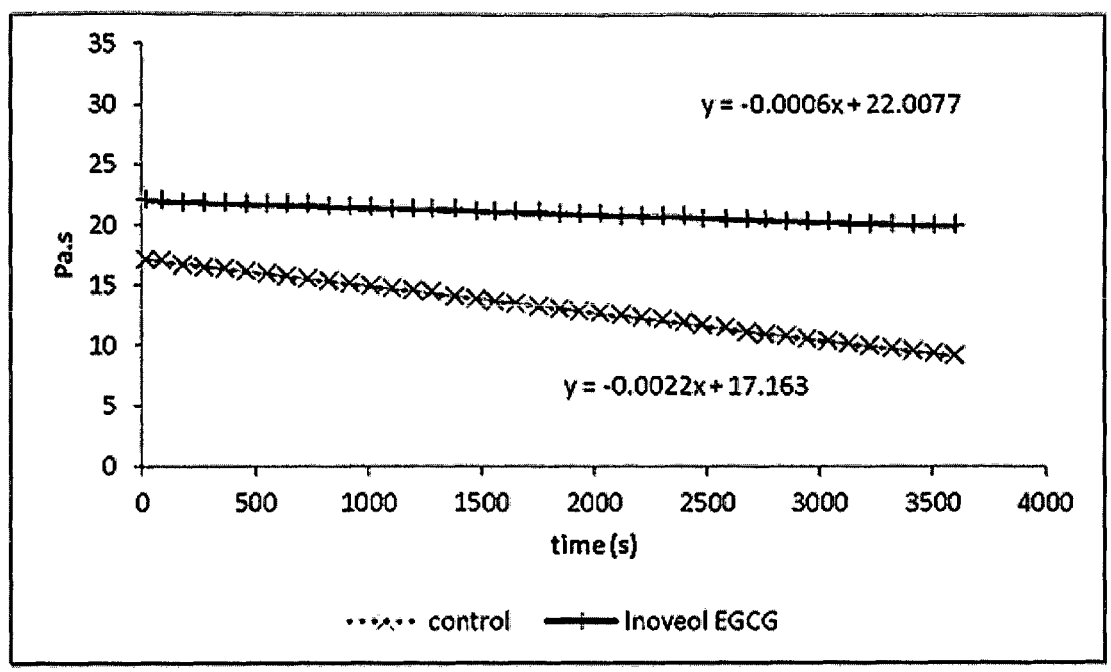
FIG. 10 is a graph illustrating experimental data obtained that shows that the gel containing Inoveol® EGCG at 0.5% (w/w) is more stable with respect to free radical degradation (ratio 2.0), than the control, even with both gels having been submitted to accelerated aging at 45° C. for 60 days prior to degradation.

A comparison of antioxidant properties after thermal stability at 45° C., 60 days for a HA-based gel matrix with 0.5% (w/w) Inoveol® EGCG (slope: −0.0006) versus the same HA-based gel matrix (slope: −0.0022 Pa) showed that the gel containing Inoveol® EGCG is more stable with respect to free radical degradation. $T_{30}$ for the HA-based gel matrix with 0.5% (w/w) Inoveol® EGCG is about 25676 seconds versus 5461 seconds for the HA-based gel matrix alone. This is about a 370% improvement due to the additive. These results are illustrated in FIG. 10.

Example 10

Use of Dermal Filler Composition for Treating Aging Skin

This Example illustrates the use of a compositions of the invention for treating aging skin.

A 44-year-old woman presents with uneven texture on her right cheek resulting from a loss of collagen due to aging. Pre-operative evaluation of the person includes routine history and physical examination in addition to thorough informed consent disclosing all relevant risks and benefits of the procedure. The physician evaluating the individual determines that she is a candidate for soft tissue treatment using a dermal filler comprising a crosslinked hyaluronic acid gel containing Caffeyl Glucoside, a derivative of caffeic acid at a concentration of 0.5% (w/w), and a HA concentration of 20 mg/mL. The composition is administered subcutaneously and under superficial musculature of the affected regions once a week for three weeks; about 3.0 mL to about 4.0 mL of composition into the affected cheek region. The individual is then monitored for approximately 7 days. The physician evaluates the facial regions and determines that the treatment was successful. Both the woman and her physician are satisfied with the results of the procedure because the texture on her face has improved. Approximately one month after the procedure, the woman indicates that her quality of life has improved.

Example 11

Use of Dermal Filler Composition for Treating Wrinkles

This example illustrates the use of compositions of the invention as a dermal filler for reducing the appearance of nasolabial folds.

A 62-year-old woman presents with deep and pronounced nasolabial folds. Pre-operative evaluation of the person includes routine history and physical examination in addition to thorough informed consent disclosing all relevant risks and benefits of the procedure. The physician evaluating the individual determines that she is a candidate for a dermal filler treatment using the a dermal filler comprising a hyaluronic acid and Epigallocatechin Gallatyl Glucoside, at a concentration of 0.5%, and a concentration of about 15 mg/mL. The composition is administered subcutaneously, using standard techniques, in an amount of about 1.5 ml under each nasolabial fold of the patient's face, through a 27 gauge needle. The individual is then monitored for approximately 14 days. The physician evaluates the facial regions and determines that the treatment was successful. Both the woman and her physician are satisfied with the results of the procedure because the nasolabial folds are less pronounced and the patient feels that she looks younger.

Although aspects of the present specification have been described with reference to the various embodiments, one skilled in the art will readily appreciate that the specific examples disclosed are only illustrative of the principles of the subject matter disclosed herein. Therefore, it should be understood that the disclosed subject matter is in no way limited to a particular methodology, protocol, and/or reagent, etc., described herein. As such, those skilled in the art could make numerous and various modifications or changes to or alternative configurations of the disclosed subject matter can be made in accordance with the teachings herein without departing from the spirit of the present specification. Accordingly, the present invention is not limited to that precisely as shown and described.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. Unless otherwise indicated, all numbers expressing quantities of ingredients, properties such as molecular weight, reaction conditions, and so forth used in the specification and claims are to be understood as being modified in all instances by the term "about." As used herein, the term "about" means that the item, parameter or term so qualified encompasses a range of plus or minus ten percent above and below the value of the stated item, parameter or term.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention.

What is claimed is:

1. A dermal filler composition comprising:
   a crosslinked hyaluronic acid-based polymer, and
   a glucosylated derivative of caffeic acid.

2. The composition of claim 1, wherein the composition is substantially stable during sterilization with a heat treatment above 100° C.

3. The composition of claim 1, wherein free radical stability of the composition is significantly increased by the addition of the glucosylated derivative of caffeic acid, with a $T_{30}$ increase of at least about 25%.

4. The composition of claim 1, wherein free radical stability of the composition is significantly increased by the addition of the glucosylated derivative of caffeic acid, with a $T_{30}$ increase of at least about 50%.

5. The composition of claim 1, wherein free radical stability of the composition is significantly increased by the addition of the glucosylated derivative of caffeic acid, with a $T_{30}$ increase of at least about 100%.

6. The composition of claim 1, wherein the composition is injectable.

7. The composition of claim 1, wherein the crosslinked hyaluronic acid-based polymer is present at a concentration of about 5 mg/g to about 40 mg/g.

8. The composition of claim 1, wherein the crosslinked hyaluronic acid-based polymer comprises both high molecular weight hyaluronan and low molecular weight hyaluronan.

9. The composition of claim 8, wherein the high molecular weight hyaluronan has a molecular weight greater than 2,000,000 Da and wherein the low molecular weight hyaluronan has a molecular weight of less than 1,000,000 Da.

10. The composition of claim 1, wherein the glucosylated derivative of caffeic acid is present at a concentration of about 0.01% (w/w) to about 5% (w/w).

11. The composition of claim 1, wherein the composition is stable after sterilization with a heat treatment at or about 100° C.

12. A method of reducing the appearance of wrinkles in skin of a patient, the method comprising administering by injection, the composition of claim 1 into the skin of the patient.

13. A cohesive injectable dermal filler composition comprising:
   a crosslinked hyaluronic acid-based polymer, and a glucosylated derivative of caffeic acid, wherein free radical stability of the composition is significantly increased by the addition of the glucosylated derivative of caffeic acid, with a $T_{30}$ increase of at least about 25%, and wherein the composition is stable after sterilization with a heat treatment at or above 100° C.

14. A method of reducing the appearance of wrinkles in skin of a patient, the method comprising administering by injection, the composition of claim 13 into the skin of the patient.

* * * * *